US006571934B1

(12) United States Patent
Thompson et al.

(10) Patent No.: US 6,571,934 B1
(45) Date of Patent: Jun. 3, 2003

(54) BI-DIRECTIONAL MAGNETIC SAMPLE RACK CONVEYING SYSTEM

(75) Inventors: David R. Thompson, Kennett Square, PA (US); Tumkur R. Vijay, Newark, DE (US); William D. Dunfee, Newark, DE (US); Daniel E. Gillund, Newark, DE (US)

(73) Assignee: Dade Behring Inc., Deerfield, IL (US)

( * ) Notice: Subject to any disclaimer, the term of this patent is extended or adjusted under 35 U.S.C. 154(b) by 51 days.

(21) Appl. No.: 09/992,917

(22) Filed: Nov. 14, 2001

(51) Int. Cl.[7] ............................................... B65G 35/00
(52) U.S. Cl. ...................................................... 198/619
(58) Field of Search ......................................... 198/619

(56) References Cited

U.S. PATENT DOCUMENTS

| | | | | |
|---|---|---|---|---|
| 2,144,835 A | * | 1/1939 | Dickinson ..................... 108/21 |
| 3,834,542 A | * | 9/1974 | Linstruth ..................... 210/222 |
| 3,952,857 A | * | 4/1976 | Nazuka ....................... 198/637 |
| 4,589,541 A | * | 5/1986 | Lisec ........................ 198/468.4 |
| 5,088,593 A | * | 2/1992 | Lewin ........................ 198/619 |
| 5,172,803 A | * | 12/1992 | Lewin ........................ 198/619 |
| 5,366,697 A | | 11/1994 | Tomasso et al. ............... 422/64 |
| 5,720,377 A | | 2/1998 | Lapeus et al. ............. 198/346.1 |
| 5,735,387 A | | 4/1998 | Polaniec et al. .......... 198/690.1 |
| 5,816,385 A | | 10/1998 | Ootsuki et al. ........... 198/690.1 |
| 5,871,084 A | | 2/1999 | Kasik ....................... 198/803.6 |
| 5,896,873 A | | 4/1999 | Furlani et al. ................. 134/32 |
| 5,906,262 A | | 5/1999 | Miki ..................... 198/341.02 |
| 6,206,176 B1 | | 3/2001 | Blonigan et al. ............ 198/619 |

* cited by examiner

Primary Examiner—Christopher P. Ellis
Assistant Examiner—Richard Ridley
(74) Attorney, Agent, or Firm—Leland K. Jordan

(57) ABSTRACT

A magnetic sample rack adapted to support liquid containers is urged along a surface by means of a magnetic conveyor system located beneath the surface. The magnetic conveyor system comprises a plurality of magnetic housings driven by a belt, the magnetic housings including a magnet slideably contained in a closed upper cavity. Magnetic forces emanating from the magnet overcome frictional resistive forces between the sample racks and the operating surface and move the sample racks along input and output lanes defined in the operating surface. Abrupt movements of the sample racks are eliminated because the housing magnet slides smoothly towards the sample rack, secures the sample rack, and pulls the rack along the operating surface as the housings are moved at a steady rate by the belt.

11 Claims, 18 Drawing Sheets

US 6,571,934 B1

BI-DIRECTIONAL MAGNETIC SAMPLE RACK CONVEYING SYSTEM

FIELD OF THE INVENTION

The present invention relates to a method and apparatus for automatically processing a patient's biological fluids such as urine, blood serum, plasma, cerebrospinal fluid and the like. In particular, the present invention provides a magnetic drive system for moving liquid samples in containers held in a rack into and out of a clinical analyzer.

BACKGROUND OF THE INVENTION

Various types of tests related to patient diagnosis and therapy can be performed by analysis assays of a sample of a patient's infections, bodily fluids or abscesses for an analyte of interest. Such patient samples are typically liquids placed in sample vials, are extracted from the vials, combined with various reagents in special reaction vessels or tubes, incubated, and analyzed to aid in treatment of the patient. In a typical clinical chemical analysis, one or two assay reagents are added at separate times to a liquid sample having a known concentration, the sample-reagent combination is mixed and incubated. Interrogating measurements, turbidimetric or fluorometric or absorption readings or the like, are made to ascertain end-point or rate values from which an amount of analyte may be determined, using well-known calibration techniques.

Although various known clinical analyzers for chemical, immunochemical and biological testing of samples are available, analytical clinical technology is challenged by increasing needs for improved levels of analysis. Automated clinical analyzers improve operating efficiency by providing results more rapidly while minimizing operator or technician error. However, due to increasing demands on clinical laboratories regarding assay throughput, new assays for additional analytes, accuracy of analytical results, and low reagent consumption, there continues to be a need for improvements in the overall performance of automated clinical analyzers. In particular, the efficiency of patient sample handling continually needs to be increased, regardless of the assay to be performed.

An important contributor to maintaining a high efficiency in throughput of patient samples is the ability to quickly and securely introduce a plurality of samples to the sample testing portion of an analyzer. Patient samples are typically held in a container such as a sample cup, a primary tube, or any other suitable container and may be open at its top or closed with a stopper or lid or the like at its top. To increase handling efficiency, the containers may then be placed into a sample rack adapted to support multiple sample containers generally in an upright orientation.

The sample rack is usually placed in an input portion of the analyzer and then moved to a location where a portion of the liquid patient sample is extracted, usually by aspiration using a hollow, needle like probe from the sample container for testing in the analyzer. Afterwards, the sample rack may be moved to temporary storage area or to an output portion of the analyzer where the user can conveniently remove the sample rack from the analyzer. It is known in the art to employ magnetic conveyor mechanisms transporting a source of a magnetic field to move sample racks having a ferromagnetic element and containing open or closed sample containers along input and output lanes. Hereinafter the term ferromagnetic is intended to mean a substance having a sufficiently high magnetic permeability to be positionally affected by a changing magnetic field. Likewise, the term magnetic is intended to mean a substance that is independently capable of generating a magnetic field.

When handling sample racks supporting open sample containers, magnetic conveyor mechanisms must be designed to gradually increase the strength of the magnetic field as the magnetic conveyor mechanism approaches a sample rack, thereby providing smooth and continuous handling of a sample rack containing open sample tubes so that the possibility of spillage is minimized. Such systems require precautions to prevent abrupt movements of a sample rack so that the possibility of spillage of liquid sample from an open container is minimized and/or so that the possibility of damage, for example from re-suspension of red blood cells, to liquid sample in a closed container is minimized. U.S. Pat. No. 5,720,377 addresses this need by providing a magnetic plate positioned at the bottom surface of a sample rack and a number of belt driven magnet assemblies moving below the surface of a tray. The magnetic field generated by the magnet assemblies attract the plates disposed in the bottom surface of the sample rack and engages the plate with sufficient force such that the sample rack moves along the tray in concert with the magnet assembly as the belts move. A portion of the plate is disposed at an angle with respect to the surface of the magnet assembly such that the magnetic force provided by the magnet assembly gradually builds as the belt moves, thereby to lower the backward acceleration of the rack as the magnet assembly first approaches the sample rack. This system, however, is not operable in two opposing directions along a single lane in the tray because the angular portion is unidirectional. Such a system has disadvantages whenever an analyzer is desired to be capable of moving sample racks in two directions along a single lane, for instance when an analyzer requires only a single sample rack input/output lane to achieve needed capacity. Such disadvantages also must be overcome when modular analyzers are linked together to increase capacity and it is necessary to convert separate input and output lanes into a pair of input or output lanes.

It is therefore desirable to provide a magnetic sample transport system and sample container rack which is capable of smoothly transitioning a sample rack containing open or closed sample containers along an operating surface from a moving state to a stationary position. It is further desirable that such a magnetic sample transport system be capable of bi-directional movement of sample racks along either an input or output lane without the necessity for additional mechanisms which increase cost and design complexity and reduce reliability. It is even further desirable that such a magnetic sample transport system have a solid operating surface so that in the event of sample liquid spillage or container breakage, liquids contained in the sample containers is prevented from flowing into and harming internal portions of the analyzer and so that the operating surface may be easily cleaned. It is finally desirable that the magnetic sample transport system have no operating mechanisms above the operating surface, other than the moving sample rack, in order to eliminate moving danger points to an operator.

U.S. Pat. No. 6,206,176 discloses a magnetic drive system for moving a substrate transfer shuttle along a linear path between chambers in a semiconductor fabrication apparatus. A rack with rack magnets is secured to the shuttle, and a rotatable pinion with pinion magnets is positioned adjacent the rack so that the pinion magnets can magnetically engage the rack magnets. Rotation of the pinion causes the shuttle to move along the linear path. The magnets may be oriented with a helix angle between their primary axis and the axis of rotation of the pinion. One rack and one pinion are located on each side of the shuttle. A set of lower guide rollers supports the shuttle, and a set of upper guide rollers prevents the shuttle from lifting off the lower guide rollers.

U.S. Pat. No. 5,906,262 provides a positioning control system to control stoppage of a conveyed article with a magnetic conveyor system element on the receiving side when a conveyed article is passed between magnetic conveyor device elements in a noncontacting magnetic conveyor system. The system comprises two independently operating magnetic conveyor system elements and two drive shafts, each of which has helical magnetic poles at its surface. The carrier is equipped with magnetic poles of equal pitch to the pitch of the helical magnetic poles. When the rotary shafts rotate, the carrier moves over the guide path by a magnetic coupling action and is passed between the magnetic conveyor system elements.

U.S. Pat. No. 5,896,873 discloses an apparatus for transporting magnetic objects using a magnetic transport roller mounted to a frame for conveying a ferromagnetic carrier, and a ferromagnetic stator for rotating the transport roller. The ferromagnetic stator is integrally associated with the transport roller which has a plurality of spatially separated pole teeth. The transport roller has a magnetic core, a first bonding layer surrounding and bonded to the core, a first layer surrounding and bonded to the first bonding layer, a second bonding layer for bonding second layer to the core. The second layer is a wear and abrasion resistant material.

U.S. Pat. No. 5,871,084 discloses a conveyor system for transporting magnetic articles along an elongate path including at least one arcuate section; a chain conveyor mounted for movement through the track; at least two grids attached to the chain conveyor, a portion of each of said grids extending laterally relative to said elongate track; at least one magnet mounted on each grid for coupling by magnetic force at least one magnetically attractable article to at least one of the grids; and a connector apparatus for allowing limited movement of the article coupled by the magnet, relative to the grid, while retaining the article in engagement with the grid.

U.S. Pat. No. 5,816,385 provides for a conveying device which is capable of conveying a magnetic piece at high speed with low vibration and low noise and which makes it possible to perform a highly accurate positioning. The conveying device includes a non-magnetic rail which has a guide surface for slidably guiding a first surface of the piece and a non-magnetic conveying belt which has a conveying surface coming into contact with a second surface of the piece and which is movable along the rail. The belt is driven to rotate by a driving device. A magnet is arranged at a position opposite to the rail with the belt therebetween and generates a magnetic force having a component force which causes the second surface of the piece to be brought into close contact with the belt and a component force which causes the first surface of the piece to be brought into contact with the rail.

U.S. Pat. Nos. 5,735,387 and 5,720,377 also address a magnetic conveyor system for transporting test samples in tubes disposed in a sample rack having a magnetic or magnetically attractive region is described. The magnetic conveyor system includes a drive system, a magnet coupled to the drive system and movable in response to the drive system and a tray having a first surface adapted to receive the sample rack. The magnet is spaced a predetermined distance from the first surface of the tray such that the magnet provides a magnetic force at the surface of the tray. The magnetic force engages the magnetically attractive region of the sample rack disposed on the tray to thereby move the sample rack along the first surface of the tray in response to movement of the drive system. When the tray reaches the end of the rack it is moved onto a processing queue tray where it is available for test purposes. A barcode reader reads a bar code on each test sample as it is placed on the process queue to identify one or more tests to perform. When all samples have received the individual tests the rack exits to an output queue for disposal. When a test must be made on an immediate basis out of normal processing order a sample rack can be inserted into the process queue via a priority rack feed.

U.S. Pat. No. 5,366,697 describes a tray and conveyor for the trays for moving liquid samples in an analyzer. The tray comprises a base having a magnetic member for responding to a magnetic field, a tray frame and member for freely rotatably mounting the frame on the base, the tray frame comprising a plurality of receptacles constructed to receive either sample tubes or aspirating tips useful to aspirate sample from a tube, the receptacles including a fixed bottom support. The conveyor comprises a support, conveying members under the support comprising a plurality of magnets and members for generating a moving magnetic field with the magnets, the conveying members being mounted in a continuous loop under the support and the support being permeable to a magnetic field, one of the above-noted trays being mounted above the support on the base.

From this discussion of the art state in automated clinical analyzers, it may be seen that while considerable progress has been made toward increasing sample handling efficiency, there remains an unmet need for a system and apparatus that provides automated handling of sample racks containing open and closed sample tubes. In particular, there remains an unmet need for a system and apparatus that provides smooth and continuous handling of a sample rack containing sample tubes in either of two mutually opposing directions so that the possibility of sample damage or spillage is minimized.

SUMMARY OF THE INVENTION

The present invention provides a magnetic sample rack adapted to support one or more open test tubes, the sample rack including a ferromagnetic plate secured in a closed base cavity and a linear transport mechanism to move sample racks along a continuous operating surface. Sample racks are urged along the top of the operating surface by means of a magnetic conveyor system located beneath the solid surface. The magnetic conveyor system comprises a plurality of magnetic housings attached to a linear transport mechanism, the magnetic housings including a housing magnet slideably contained in a closed upper cavity section. The magnetic housings are sufficiently proximate the magnetic sample rack so that magnetic forces emanating from the housing magnet overcome frictional resistive forces between the sample racks and the operating surface and move the sample racks along input and output lanes defined in the operating surface. Abrupt movements of the sample racks are eliminated because the magnet slides smoothly within its housing towards the sample rack, secures the sample rack, and pulls the rack along the operating surface as the housings are moved at a steady rate by the pulley driven belt. Consequently, the sample rack smoothly transitions from a stationary position to a moving state minimizing the potential for fluid spillage from an open sample container.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
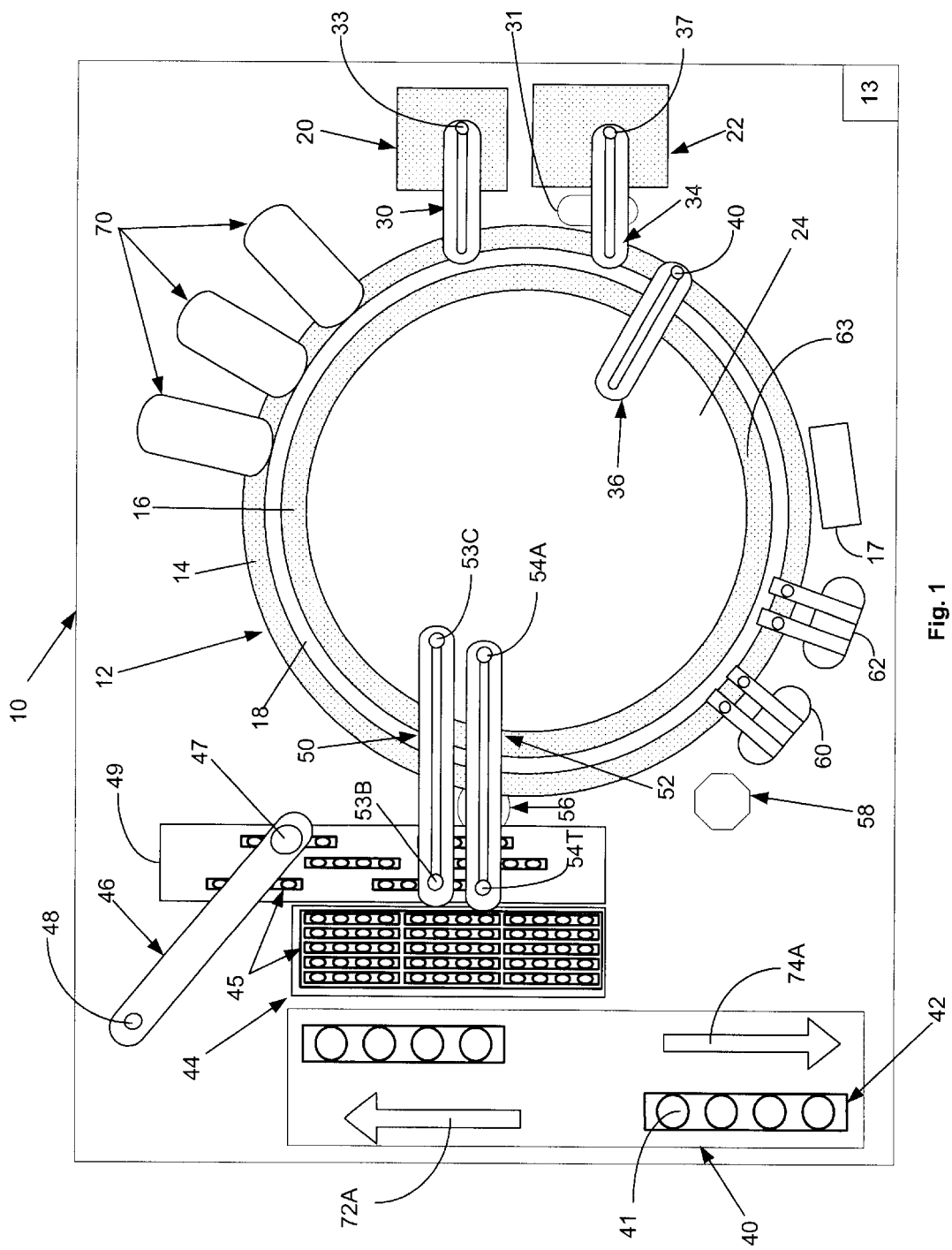
FIG. 1 is a schematic plan view of an automated analyzer in which the present invention may be used to advantage.
Figure 2:
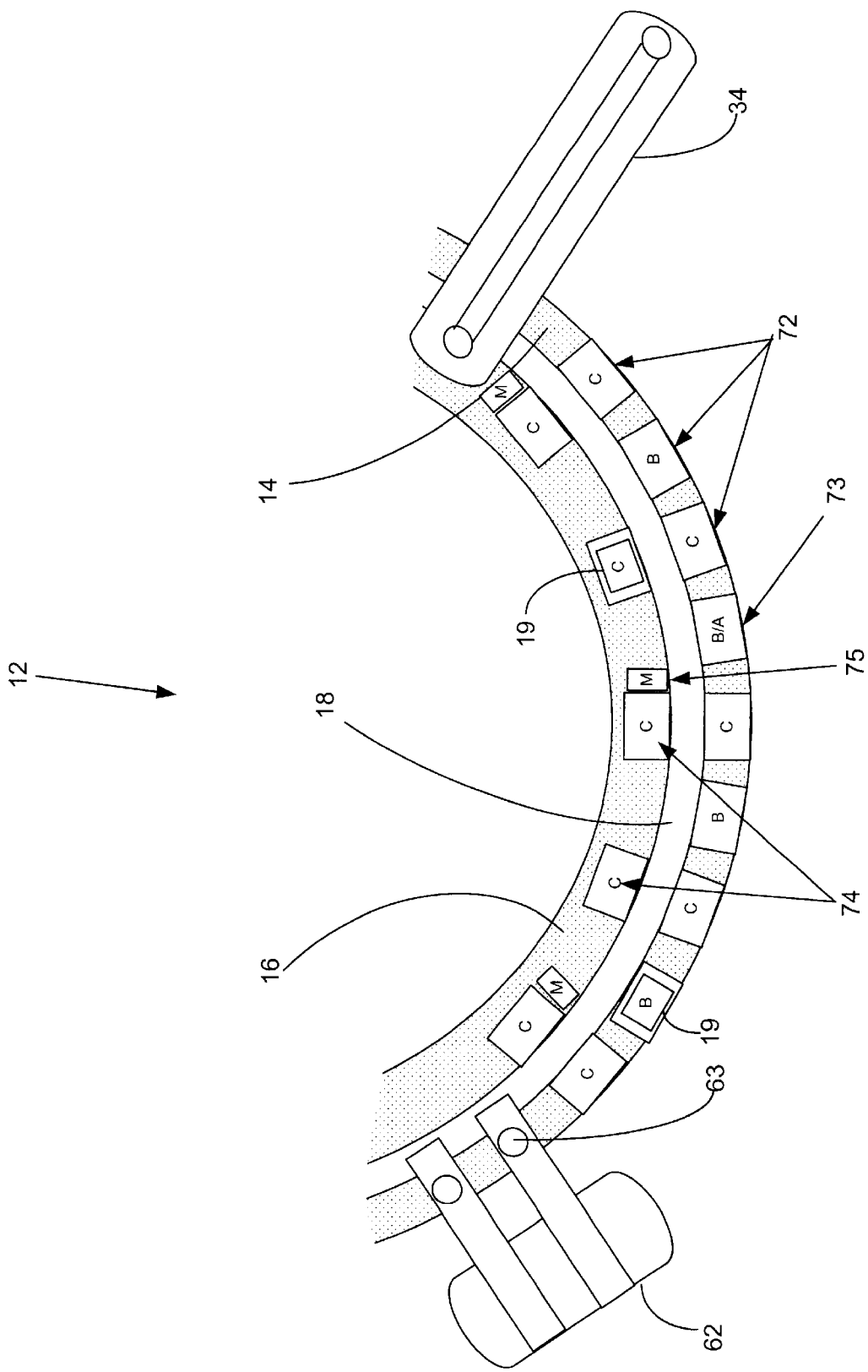
FIG. 2 is an enlarged partial schematic plan view of the automated analyzer of FIG. 1.

FIG. 1, taken with FIG. 2, shows schematically the elements of a conventional automatic chemical analyzer 10 in which the present invention may be advantageously practiced. Analyzer 10 comprises a reaction carousel 12 supporting a outer cuvette circle 14 of cuvette ports 72 and 73 and an inner cuvette circle 16 of cuvette ports 74, the outer cuvette circle 14 and inner cuvette circle 16 being separated by a open groove 18. Cuvette ports 72, 73 and 74 are adapted to receive a plurality of reaction cuvettes 19 typically formed as small, flat walled, U-shaped containers with an open central reaction portion closed at the bottom and with an opening at the top of the cuvettes 19 to allow the addition of reagent and sample liquids. Reaction carousel 12 is rotatable using stepwise movements in a constant direction at a constant velocity, the stepwise movements being separated by a constant dwell time during which dwell time, carousel 12 is maintained stationary and an assay device located proximate carousel 12 may operate on an assay mixture contained within a cuvette 19.

Figure 3:
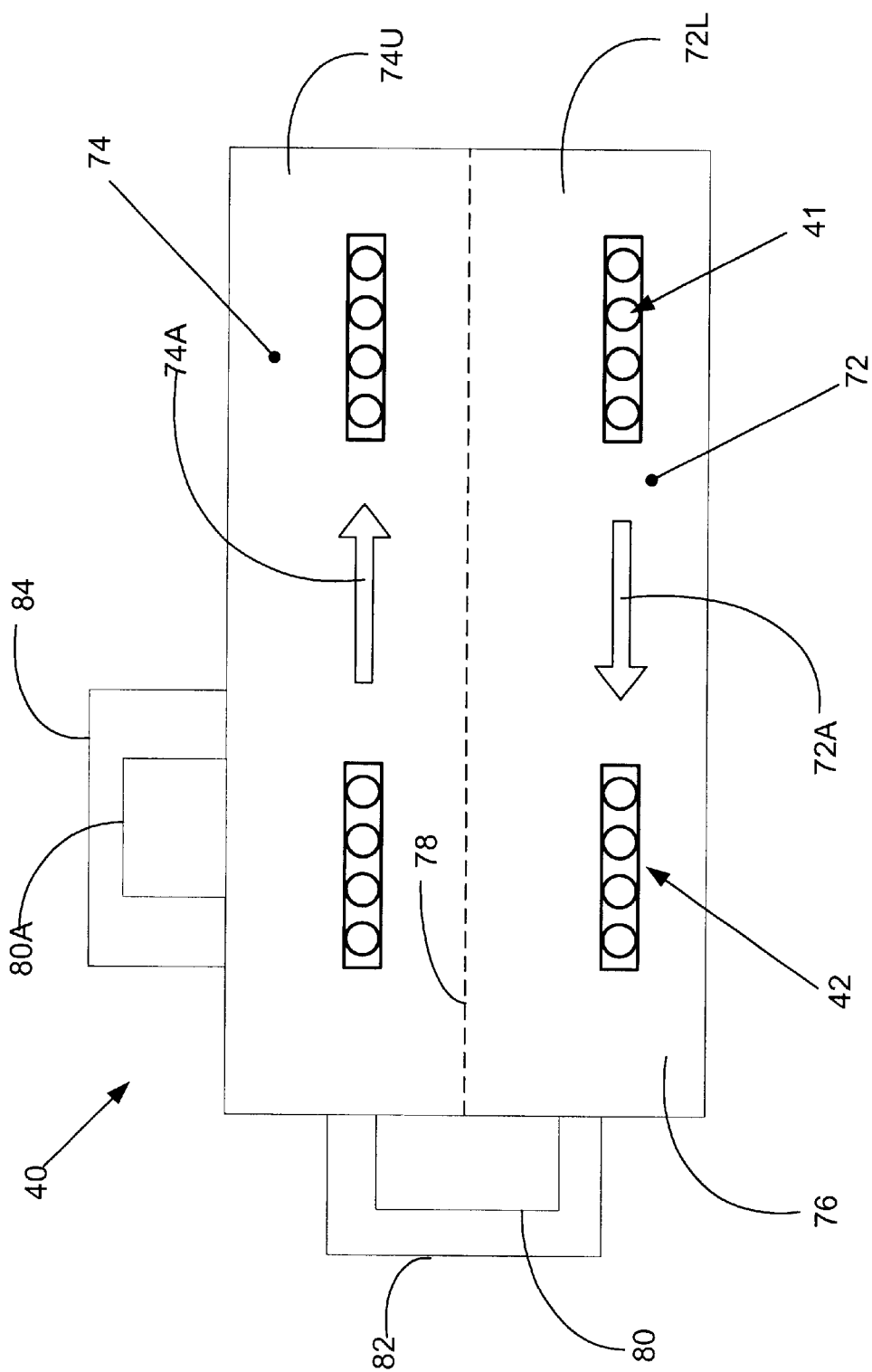
FIG. 3 is schematic top plan view of the magnetic drive system of the present invention.

Three temperature-controlled reagent storage areas 20, 22 and 24 each store a plurality of reagent cartridges 21, cartridges 21, for example being a multi-compartmented reagent container like those described in U.S. Pat. No. : 4,720,374, sold under the tradename FLEX® reagent cartridge by Dade Behring Inc, Deerfield, Ill., and containing reagents as necessary to perform a given assay. A selectively-opened lid (not shown) covers each of reagent storage areas 20, 22 and 24 to allow access to cartridges 21; for simplicity, only three reagent cartridges 21 are schematically illustrated in FIG. 3 as disposed beneath a cut out portion of reagent storage area 24, however similar reagent cartridges 21 are disposed within reagent storage areas 20 and 22. Shuttle means (not shown) move individual cartridges 21 to probe access ports. Storage areas 20 and 22 may be conveniently located external to the circumference of outer cuvette circle 14 and reagent storage area 24 may be conveniently located internal to the circumference of inner cuvette circle 16.

A clinical analyzer 10 like those on which the present invention may be performed has a plurality of conventional assay operation stations disposed proximate carousel 12 and at which are positioned individual computer controlled electro-mechanical devices, such as sensors, reagent add stations, mixing stations, and the like, as required to perform the myriad of actions required in well known clinical assays. Such devices and their operation are well known in the art and need not be described herein. See for example, U.S. Pat. Nos. 5,876,668, 5,575,976 and 5,482,861 and the references cited therein.

An indexing drive for the reaction carousel moves the reaction vessels in the constant direction a predetermined numbers of incremental steps. The length of the circumference of cuvette circle 14, the separation distance between cuvette ports 72, 73 and 74, the number of cuvette ports 72, 73 and 74, and the number of increments per indexing are selected so that any given cuvette ports 72, 73 or 74 returns to its original starting position after a fixed number of incremental steps. A number of liquid aspiration and dispense arms 30, 34, and 36 are located proximate the reagent storage areas 20, 22 and 24 and controlled by a programmed computer 13, preferably a microprocessor based central processing unit (CPU) to control all activities of analyzer 10 according to pre-programmed software, firmware, or hardware commands or circuits.

Cuvette load and unload stations 60 and 62 are positioned proximate outer cuvette carousel 14 and are conventionally adapted to load cuvettes 19 into cavities 72, 73 and 74 seen in FIG. 2 formed in both outer cuvette carousel 14 and inner carousel 16 using for example a translatable robotic clamp 63. Conventional sample processing devices, or stations 17 are positioned at selected circumferential locations about the reaction carousel 12 in order to access reaction vessels 19. Stations 17 are adapted to provide, among other processing steps, for mixing together of the sample liquid and the reagent liquid contained in a cuvette 19, for washing the sample liquid and the reagent liquid contained in a cuvette 19, and for magnetic separation of tagged magnetic particles from free tags or reagent liquid contained in a cuvette 19.

Incoming sample specimens to be tested are transported by a sample tube rack transport system 40 and inventoried within analyzer 10 inside an environmental chamber 44 described in co-pending application Ser. No.: 09/827,045 assigned to the assignee of the present invention. Specimens are typically contained in open sample containers or tubes 41 supported in sample tube racks 42 and are identified by reading bar coded indicia on sample tubes 41 using a conventional bar code reader to determine, among other items, a patient's identity, the tests to be performed, if a sample aliquot is desired to be retained inside environmental chamber 44 and if so, for what period of time.

A sampling arm 46 supports a conventional liquid sampling probe 47 and is mounted to a rotatable shaft 48 so that movement of sampling arm 46 describes an arc intersecting the sample tube transport system 40 and an aliquot strip transport system 49 adapted to transport aliquot strips 45 to a pair of conventional sample/reagent aspiration and dispense arms 50 and 52 located proximate reaction carousel 12. Sampling arm 46 is operable to aspirate liquid sample from sample tubes 41 and to dispense a sample aliquot into one or more of a plurality of wells in aliquot strips 45, depending on the quantity of sample required to perform the requisite assays and to provide for a sample aliquot to be retained by analyzer 10 within environmental chamber 44. After sample has been dispensed into cuvettes, conventional transfer means move aliquot strips 45 as directed between aliquot strip transport system 49 and storage compartment 44.

Various assay analyzing means 70 may be located proximate outer cuvette carousel 14 and are adapted to measure light absorbence in or emission from cuvettes 15 at various wavelengths, from which the presence of analyte in the sample liquid may be determined using well-known analytical techniques. Means 70 typically comprise conventional photometric, fluorometric or luminescent measuring devices adapted to perform an interrogating measurement at any convenient time interval during which reaction carousel 12 is stationary.

Drive means are provided for independently rotating outer reaction carousel 12 about an axis, the drive means typically comprising gear teeth disposed on the carousel 12 and interlacing with pinion gears mounted on the shaft of a motor. The drive means may be of conventional design and are not illustrated.

Analyzer 10 is controlled by computer 13 based on software written in a machine language, like that used on the Dimension® clinical chemistry analyzer sold by Dade Behring Inc, of Deerfield, Ill., and widely used by those skilled in the art of computer-based electromechanical control programming.

As seen in FIG. 3, the sample tube rack transport system 40 includes an input lane 72 and an output lane 74 formed along a top operating surface 76 of analyzer 10. For the purpose of illustration only, input lane 72 and output lane 74 are shown separated on operating surface 76 by a dashed line 78. Input lane 72, taken with a magnetic drive system 90 described hereinafter, moves racks 42 containing open or closed sample containers such as sample tubes 41 from a rack input load position 72L at a first end of the input lane 72 right-to-left along the length of input lane 72 as indicated by open arrow 72A. Sampling arm 46 (not shown) is located proximate a second end of the input lane 72 opposite the first end of lane 72. Once a rack 42 containing sample tubes 41 is proximate sampling arm 46, the rack 42 may be held in a stationary position by a shuttle mechanism 80 in a sampling zone 82 while sampling probe 47 (not shown) aspirates liquid sample from sample tubes 41 and dispenses an aliquot portion of the sample into one or more wells in aliquot strips 45. Alternately and preferably, once a rack 42 is proximate sampling arm 46, rack 42 may be shuttled to a sample buffer zone 84 by an alternate shuttle mechanism 80A and held in a stationary position inside the buffer zone 84 while sampling probe 47 aspirates liquid sample from sample tubes 41.

When the sample tubes are at load position 72L or anywhere along input lane 72, a bar code reader typically deciphers a bar code attached thereto and transmits information to a computer 13 which performs a variety of functions including tracking the sample tubes and scheduling the order in which samples are to be assayed.

After liquid sample is aspirated from all sample tubes 41 on a rack 42 and dispensed into aliquot wells, the sample rack may optionally be held in the held in the buffer zone 84 until a successful assay result is obtained. Regardless of whether sample racks are held in the sampling zone 82 or buffer zone 84, once each sample tube 41 in a sample rack 42 has been aspirated, shuttle mechanism 80 or shuttle mechanism 80A positions the sample rack 42 onto output lane 74. Output lane 74, taken with magnetic drive system 90, moves racks 42 containing open sample tubes 41 from sampling zone 82 or buffer zone 84 toward the rightmost end of the input lane 74 as indicated by open arrow 74A to a frontal area of analyzer 10 which is readily accessible by an operator so that racks 42 may be conveniently removed from analyzer 10.

Figure 3A:
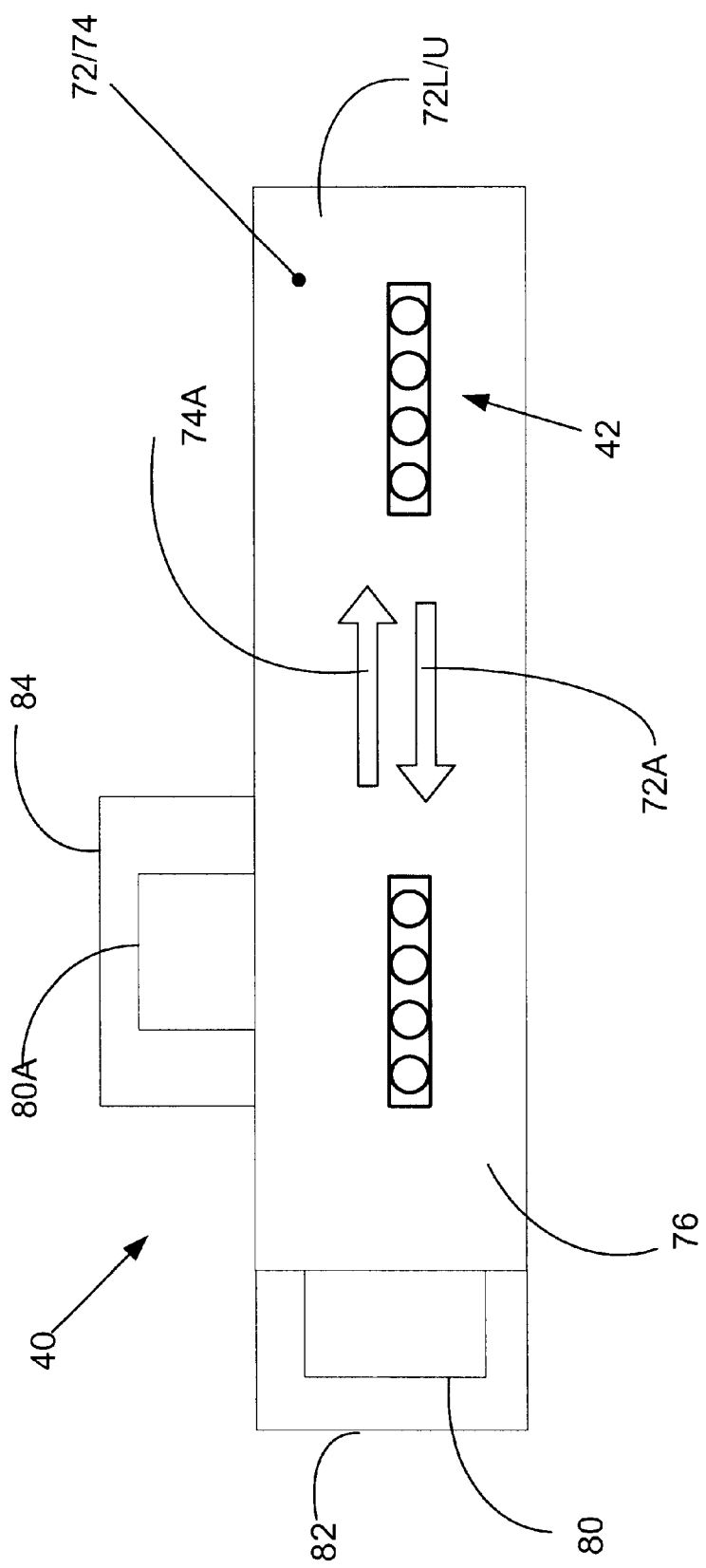
FIG. 3A is schematic top plan view of an alternate embodiment of the magnetic drive system of the present invention.

In an alternate embodiment, seen in FIG. 3A, the sample tube rack transport system 40 includes a single input-output lane 72/74 formed along operating surface 76, and when taken with a bi-directional magnetic drive system 90 described hereinafter, moves racks 42 containing sample tubes 41 from a load/unload position 72L/U at a first end of the input-output lane 72/74 right-to-left along the length of input-output lane 72/74 as indicated by open arrow 72A. Again, sampling arm 46 (not shown) is located proximate a second end of the input-output lane 72/74 opposite the first end of input-output lane 72/74. Once a rack 42 is proximate sampling arm 46, rack 42 may be shuttled to a sample buffer zone 84 by an alternate shuttle mechanism 80A and held in a stationary position inside the buffer zone 84 while sampling probe 47 aspirates liquid sample from sample tubes 41.

After liquid sample is aspirated from all sample tubes 41 on a rack 42 and dispensed into aliquot wells, shuttle mechanism 80A positions the sample rack 42 onto input-output lane 72/74. Input-output lane 72/74, taken with magnetic drive system 90, moves racks 42 containing sample tubes 41 from sampling zone 82 or buffer zone 84 toward the rightmost end of the load/unload position 72L/U at a first end of the input-output lane 72/74 as indicated by open arrow 74A to a frontal area of analyzer 10 which is readily accessible by an operator so that racks 42 may be conveniently removed from analyzer 10.

Figure 4:
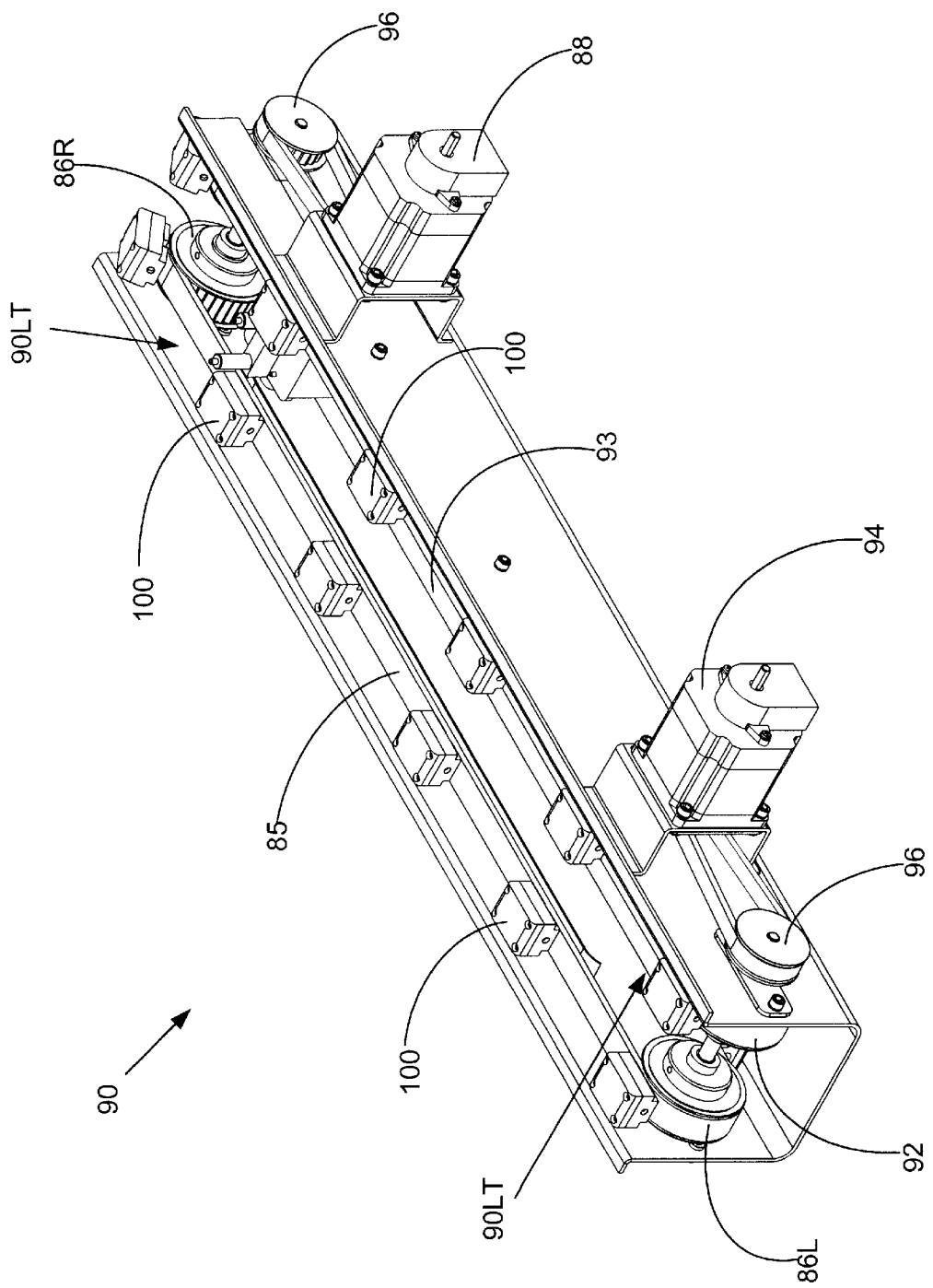
FIG. 4 is a perspective illustration of the magnetic drive system of FIG. 3.

The magnetic drive system 90 of the present invention is first seen in the perspective drawings of FIG. 4 to comprise at least one bi-directional linear drive transport mechanism 90LT depicted, for example, as a first belt 85 endlessly circulating around a first pair of pulleys 86, one of the first pulleys 86 being coupled to a first bi-directional motor 88, the first belt 85 and first pulleys 86 being mounted beneath and in close proximity to top operating surface 76 which defines input lane 72 and output lane 74. FIG. 4 illustrates two such bi-directional linear drive transport mechanisms 90LT, however, in the alternate embodiment described previously in which a single input-output lane 72/74 is employed, only a single bi-directional linear drive transport mechanism 90LT is required to practice the present invention. It should be understood that any of several mechanisms are capable of providing the bi-directional linear drive transport mechanism 90LT used within the present invention, for instance a bi-directional motor coupled to a linear drive screw, or a pneumatic operated plunger, both supporting the magnetic housings and having a moveable magnet therein as provided by the present invention. For the sake of convenience, the present invention will be described in terms of belts and pulleys but is not intended to be limited thereby.

First belt 85 is driven by motor 88 in a first direction, for example along the direction of arrow 72A, and is located beneath the input lane 72 portion of top operating surface 76. In a similar manner, magnetic drive system 90 comprises a second belt 93 endlessly circulating around a second pair of pulleys 92, one of the second pulleys 92 (only one such pulley 92 is visible) being coupled to a second bi-directional motor 94, the second belt 93 and second pulleys 92 being mounted beneath and in close proximity to the output lane 74 portion of top operating surface 76. Second belt 93 is driven by second motor 94 in a second direction opposite to the first direction. Motors 88 and 94 are typically stepper motors independently controlled by computer 13 and have drive gears 96 coupled to pulleys 86 and 92 which are preferably formed as pulley gears interlaced with gear teeth formed on belts 85 and 93. The magnetic drive system 90 is described here in terms of a pulley-and-belt drive mechanism, however, any of a number of bi-directional linear drive mechanisms may be employed to achieve the purpose of linearly moving a magnetic housing described hereinafter in either of two opposing directions.

Figure 5:
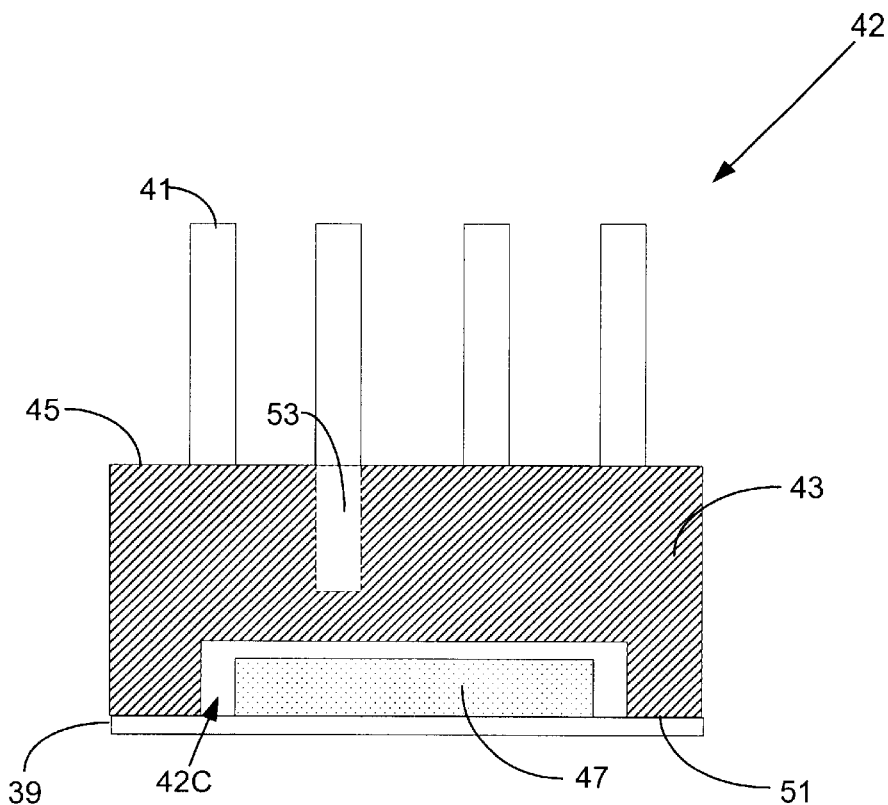
FIG. 5 is a schematic sectional view of a sample rack used in the present invention.

As best seen in FIG. 5, the sample rack 42 of the present invention is illustrated in an "upright" orientation as comprising a body portion 43 having an upper surface 45 adapted to support one or open sample tubes 41, the sample rack 42 further including a ferromagnetic plate 47 secured within a base cavity 42C formed in a lower surface 51 of sample rack 42 opposite the upper surface 45. Base cavity 42C is preferably recessed so that only as surface portion around the periphery of rack 42 rests on operating surface 76; alternately, base cavity 42 may be closed with a thin base sheet 39 of low friction material like polypropylene. Sample tubes 41 are maintained in an upright orientation within a number of closed bores 53 formed in body portion 43 so that the openings of sample tubes 41 are uppermost to prevent spillage of any liquids contained therein.

Figure 6:
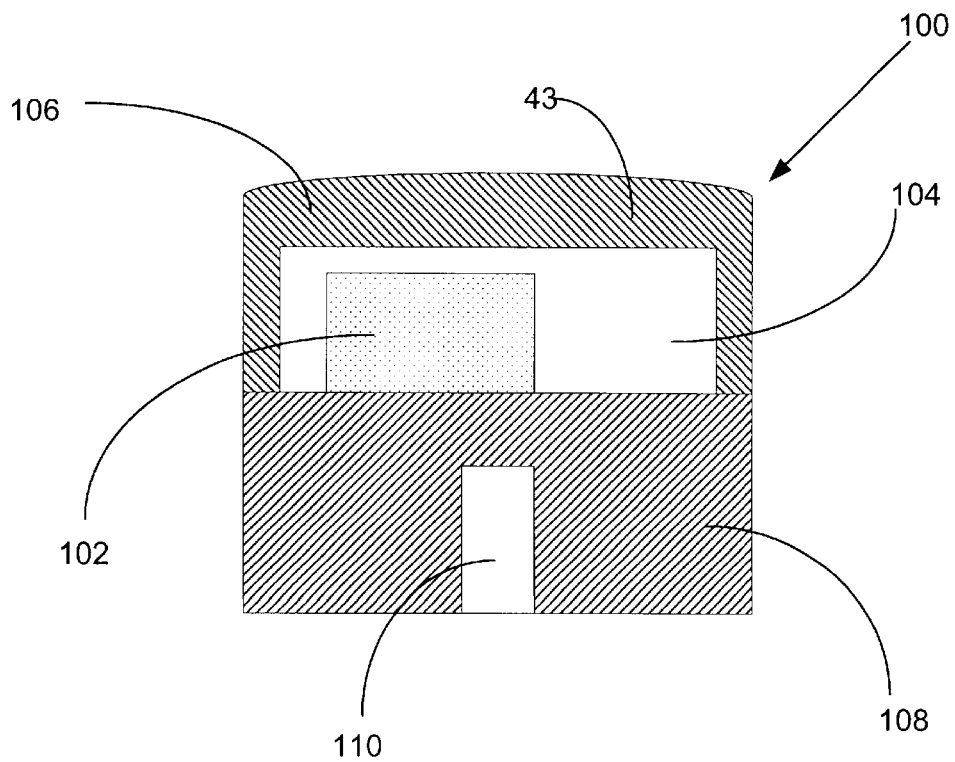
FIG. 6 is a schematic sectional view of a magnetic housing used in the present invention.

FIG. 6 illustrates a magnetic housing 100 including a housing magnet 102 moveably secured in a magnet cavity 104 located in an upper magnetic housing portion 106 of magnetic housing 100. Magnet cavity 104 is closed on the bottom by a lower magnetic housing portion 108 of magnetic housing 100, the lower magnetic housing portion 108 being secured to the upper magnetic housing portion 106 using screws or the like. A key feature of the present invention is magnet 102 being freely moveable within magnet cavity 104, in particular being freely slideable along the surface of lower magnetic housing portion 108 that closes magnet cavity 104. The housing 100 further includes a closed bore 110 extending from a generally flat bottom surface upwards as shown a partial distance into the body of the lower magnetic housing portion 108; bore 110 is provided so as to secure the magnetic housing 100 to belts 85 and 93.

Figure 7:
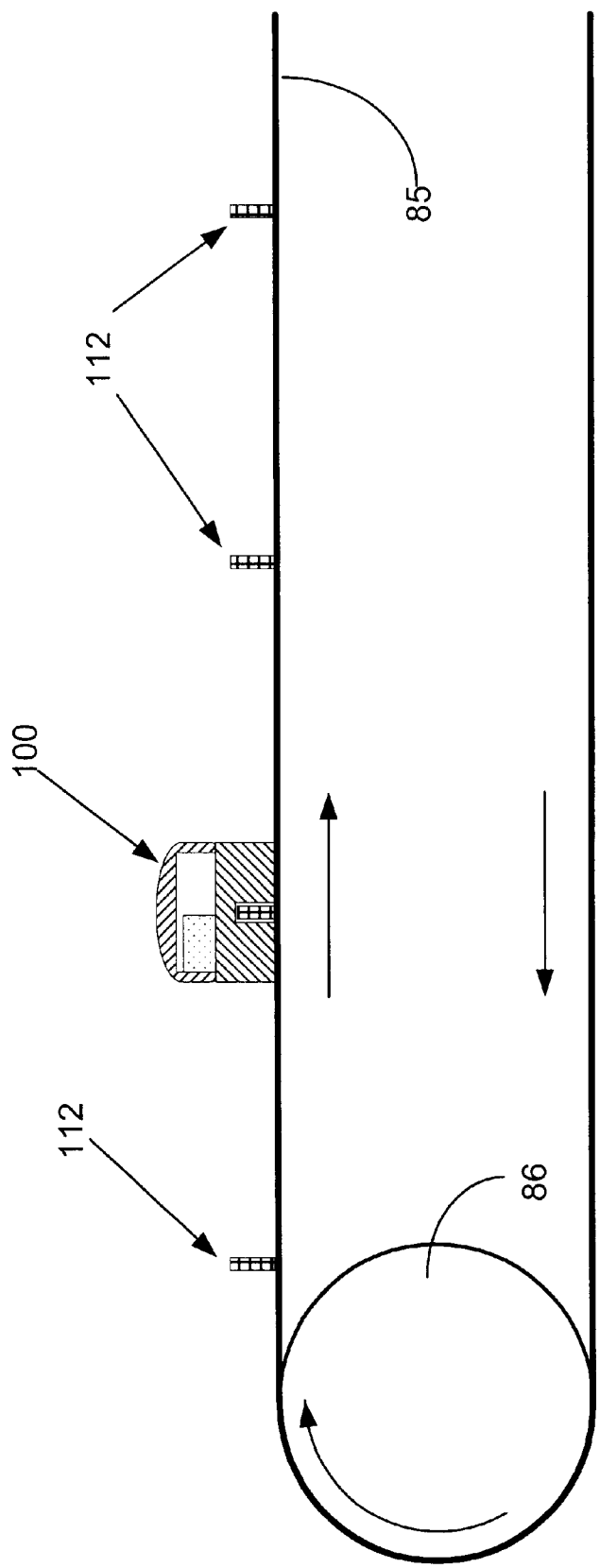
FIG. 7 is schematic elevation view of the magnetic drive system of the present invention.

FIG. 4 illustrates a plurality of magnetic housings 100 coupled to each drive belt 85 and 93. Magnetic housings 100 are coupled to belts 85 and 93 by means of a plurality of upright posts 112 generally equally spaced apart by a predetermined distance, and, as seen in FIG. 7, the plurality of upright posts 112 are attached to belts 85 and 93 at that same predetermined distance. Posts 112 are adapted by any of various mechanical techniques, such as screws, snaps, welds, etc., to secure the plurality of magnetic housings 100 to belt 85 and 93.

Belts 85 and 93 are positioned at a distance below surface 76 selected such that the attracting magnetic forces between magnets 102 and plates 47 are of sufficient strength that sample racks 42 are magnetically coupled to the magnetic housings 100. Consequently, as the magnetic housings 100 are driven along the directions of arrows 72A and 74A (FIGS. 1 and 3) by belts 93 and 85, respectively, sample racks 42 are moved along the operating surface 76 of analyzer 10. It is well within the range of skills known in that art to adjust a number of design and operating characteristics of analyzer 10, and in particular within sample tube rack transport system 40, so that computer 13 automatically controls the presentation of sample tubes 41 to liquid sampling probe 47 as required to perform the assays desired on patient samples in sample tubes 41. Important design and operating characteristics include the magnetic field strength of magnet 102, preferably a neodymium-iron-boron magnet, relative to the magnetic susceptibility of plate 47 and the size and weight of a fully loaded sample rack 42. Frictional forces between materials of construction of surface 76, optionally coated with polytetrafluorethylene, and base sheet 39 must be included in selecting such design and operating characteristics. The magnetic housings 100 can be coupled to posts 112 and the posts to belts 85 and 93 via screws or epoxy or welding techniques well known to those of ordinary skill in the art.

As mentioned earlier, an important feature of the present invention is magnet 102 being freely moveable within magnet cavity 104, in particular being freely slideable along the surface of lower magnetic housing portion 108 that closes magnet cavity 104. FIGS. 8–15, described using well-understood relative terms having their normal meanings, illustrate how magnet 102 operates within cavity 104 to smoothly transition sample rack 42 between stationary locations and sliding motions along surface 76, thereby ensuring that liquids in sample tubes 41 are not subjected to abrupt movement that may cause spillage or damage the sample liquid, for example by re-suspension of blood cells.

Figure 8:
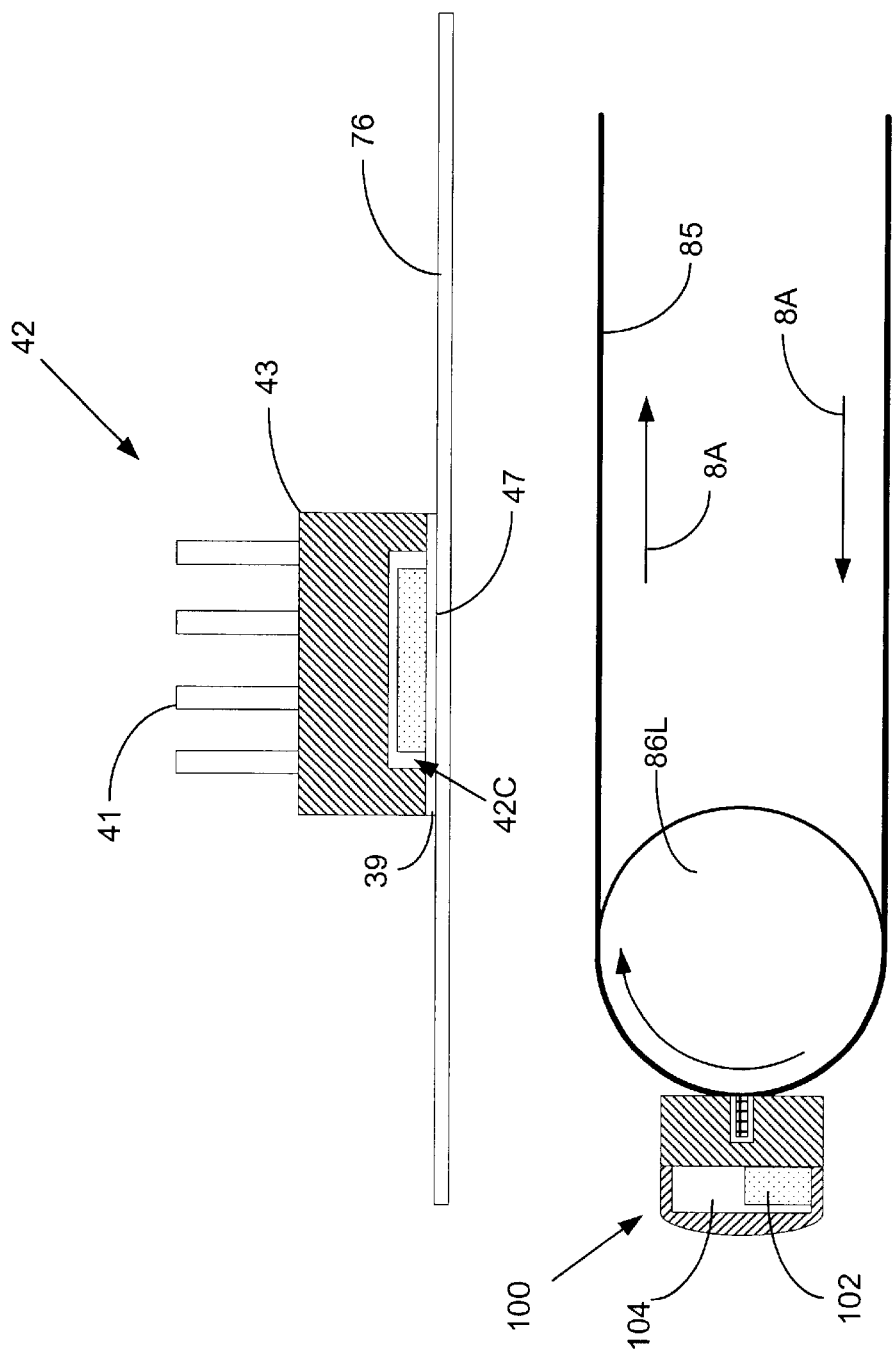
FIG. 8 is schematic elevation view of the magnetic drive system of FIG. 4 illustrating the sample rack of FIG. 5 and the magnetic housing of FIG. 6 in the first of a series of illustrations of the present invention in use.
Figure 9:
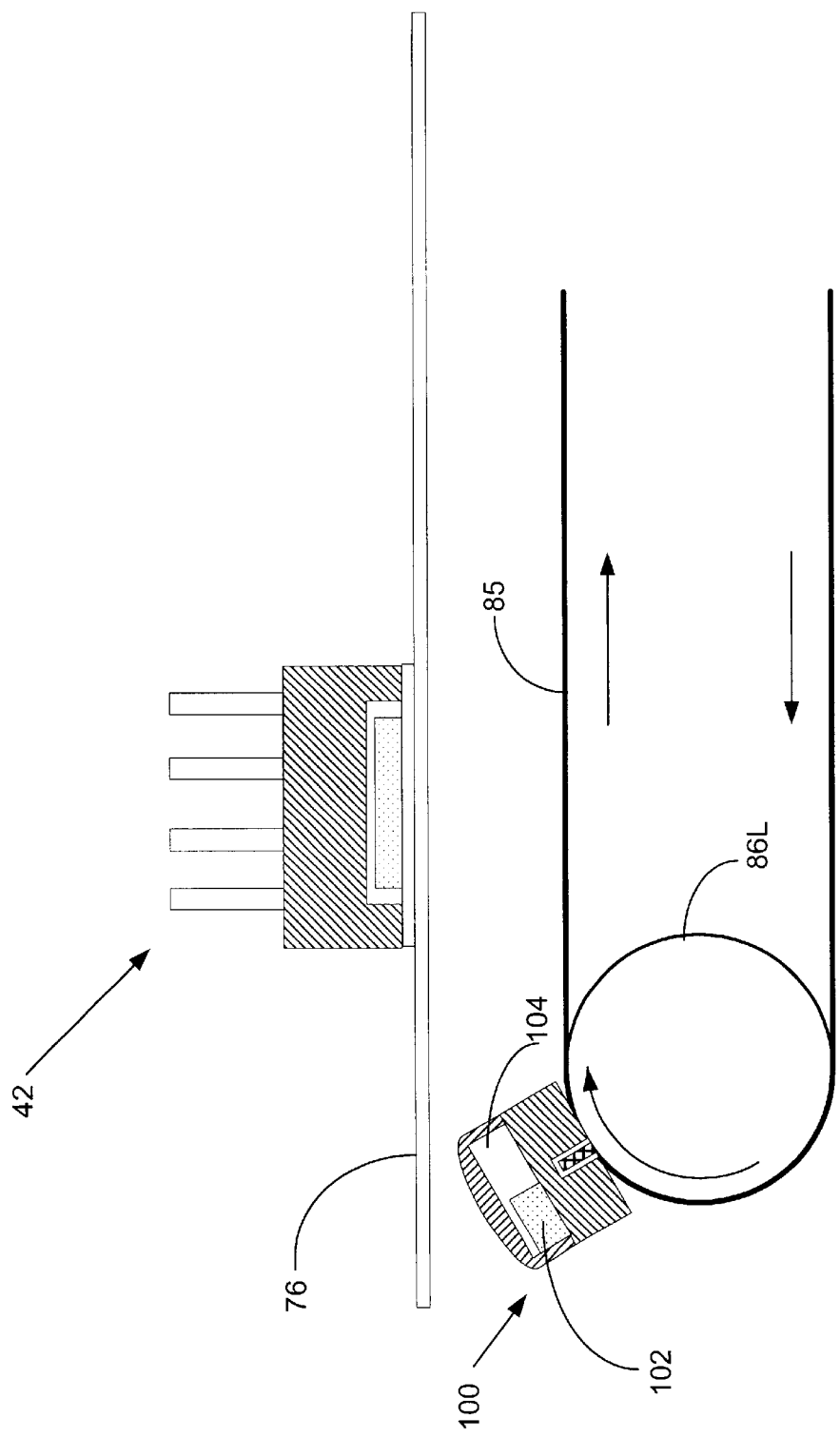
FIG. 9 is schematic elevation view of the magnetic drive system of FIG. 4 illustrating the sample rack of FIG. 5 and the magnetic housing of FIG. 6 in the second of a series of illustrations of the present invention in use.
Figure 9A:
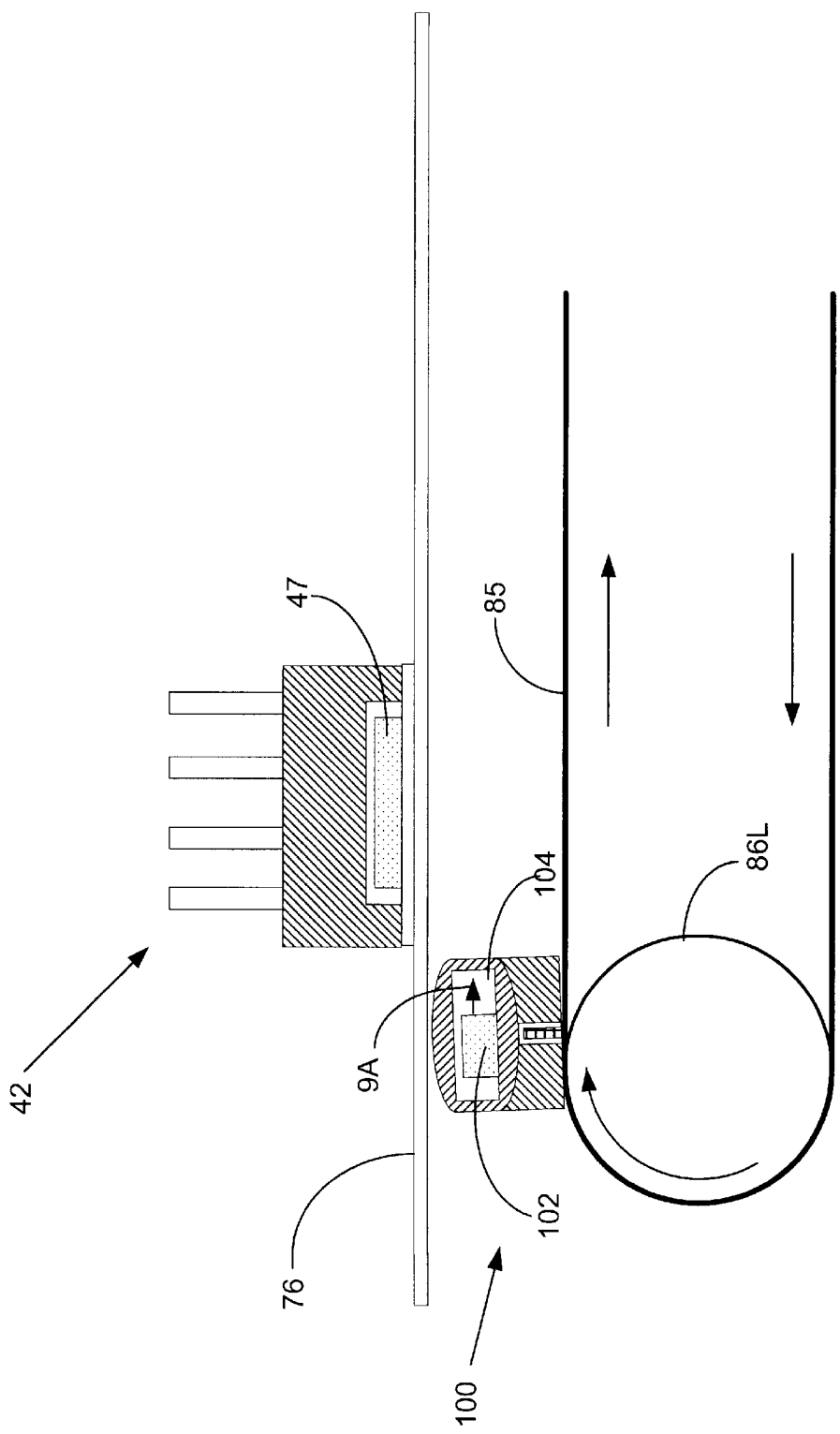
FIG. 9A is schematic elevation view of the magnetic drive system of FIG. 4 illustrating the sample rack of FIG. 5 and the magnetic housing of FIG. 6 in the third of a series of illustrations of the present invention in use.

For the sake of illustration, consider a single stationary sample rack 42 as seen supported on operating surface 76 in FIG. 8 and a single magnetic housing 100 being moved around pulley 86L driving belt 84, representative a of linear drive mechanism rotating in a left-to-right direction, as indicated by arrows 8A. In its extreme leftmost location on pulley 86L, due to gravitational forces acting on magnet 102, magnet 102 is "lowermost" within cavity 104 against what is described hereinafter as the left-hand side of cavity 104. As belt 85 is moved toward the right, it comes to a semi-horizontal orientation like seen in FIG. 9. Continued movement of belt 85, seen in FIG. 9A, brings magnetic housing 100 closer to rack 42 so that magnet 102 is drawn toward the right-hand side of cavity 104, depicted by arrow 9A, towards the right-hand side of cavity 104 due to magnetic attraction between magnet 102 and stationary ferromagnetic plate 47. As movement of belt 85 continues, magnetic housing 100 reaches a horizontal orientation and into the general proximity of sample rack 42 like seen in FIG. 10 where the left-hand side of magnet 102, now drawn against the right-hand side of cavity 104 due to magnetic attraction from stationary ferromagnetic plate 47, is generally aligned perpendicularly with the left-hand side of plate 47. Sample rack 42 is still not moved from its original stationary position, however from the situation depicted in FIG. 10 onwards, as belt 84 is driven rightwards, magnet 102 will begin to slide towards the left-most side of cavity 104 inside housing 100 because of magnetic attraction to ferromagnetic plate 47 in rack 42. Once magnet 102 has fully contacted the leftmost side of cavity 104, magnet 102 will be moved rightwards by housing 100 as belt 84 is driven rightwards, causing sample rack 42 to also be moved rightwards, "following" magnet 102, as depicted by an arrow 42A in FIG. 11. The "magnetic pulling force" between magnet 102 and plate 47 increases gradually as housing 100 is moved rightwards by belt 84 until such force reaches a maximum value when the rack 42 and magnet 102 are in the relative positions depicted in FIG. 11.

Figure 10:
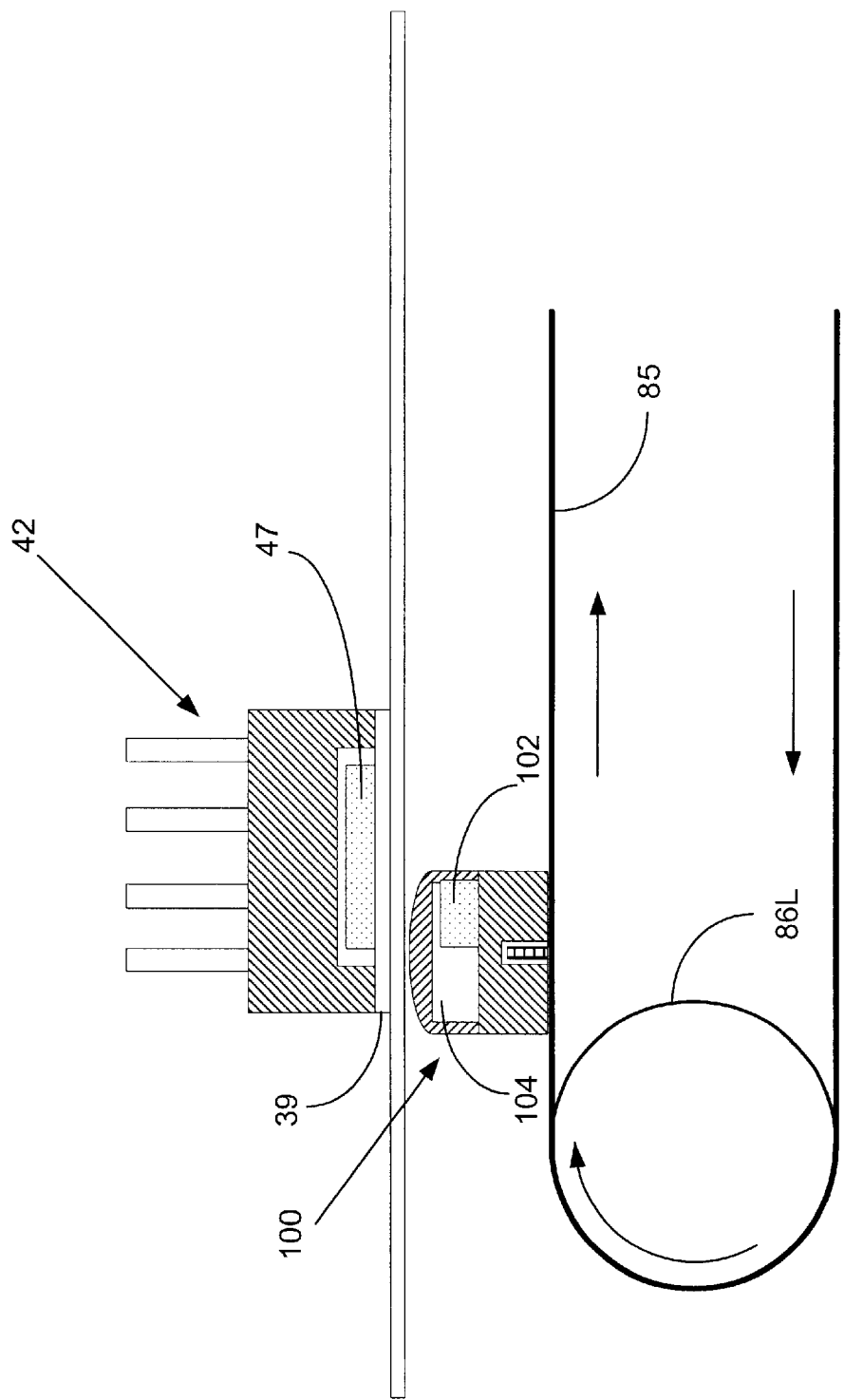
FIG. 10 is schematic elevation view of the magnetic drive system of FIG. 4 illustrating the sample rack of FIG. 5 and the magnetic housing of FIG. 6 in the fourth of a series of illustrations of the present invention in use.
Figure 11:
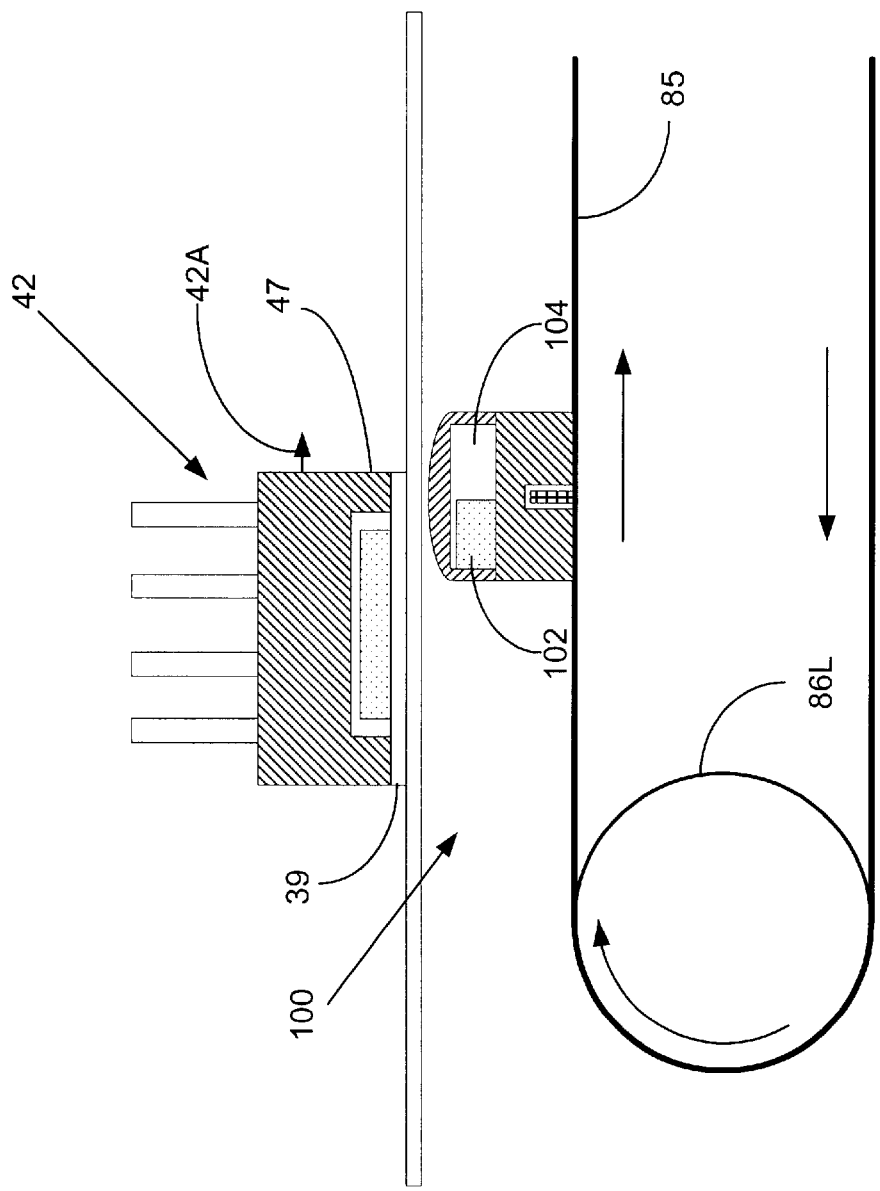
FIG. 11 is schematic elevation view of the magnetic drive system of FIG. 4 illustrating the transition of the sample rack of FIG. 5 from a stationary position to a moving stage as provided by the present invention.

In practicing the present invention, an artesian would employ well-known techniques to adjust the magnetic susceptibility of plate 47, the magnetic field strength of magnet 102, the resistive frictional forces between surface 76 and rack 42, and the distances that separate rack 42 and housing 100 so that the magnetic forces between plate 47 and magnet 102 overcome frictional forces between surface 76 and rack 42 so that rack is smoothly and continuously transitioned from a stationary position to a moving state, indicated by arrow 42A in FIG. 11, thereby minimizing the potential for fluid spillage from an open sample container. It should be appreciated that it is the combination of magnet 102 sliding inside cavity 104 and movement of magnetic housing 100 that allows the magnet 102 to move under the stationary rack 42 instead of rack 42 moving towards the magnet 102. As described earlier, as housing 100 continues to move, magnet 102 slides back to its original left-most location within cavity 104, thereby smoothly and continuously increasing the pulling force on the rack 42 and smoothly and continuously changing rack 42 from a stationary position to a moving state. Another key advantage of the slideable magnet 102 of the present invention is the elimination of "backwards" motion of the sample rack 42 as the magnet 102 approaches sample rack 42. For example, in FIG. 10, if magnet 102 was not slideably moveable but was affixed stationary to post 112, a technique employed in prior art drive systems, as magnet housing 100 approached sample rack 42 from the left, the sample rack 42 would tend to move left-wards due to the attraction of non-movable magnet 102. However, since magnet 102 is free to move in cavity 104 as shown between FIGS. 9 and 10, the initial shift in location when transitioning sample rack 42 from a stationary position to a moving state is performed by the magnet 102, not sample rack 42, thereby ensuring that the transition is smooth and continuous. (Gravity ensures that magnet 102 always approaches rack 42 with room to move with in cavity 104 as housing 100 rounds pulley 86L.). It is the initial motion of magnet 102 that reduces or eliminates any unnecessary motion of sample rack 42 which could result in undesirable spillage or re-suspension of liquids contained within sample containers 41.

Figure 12:
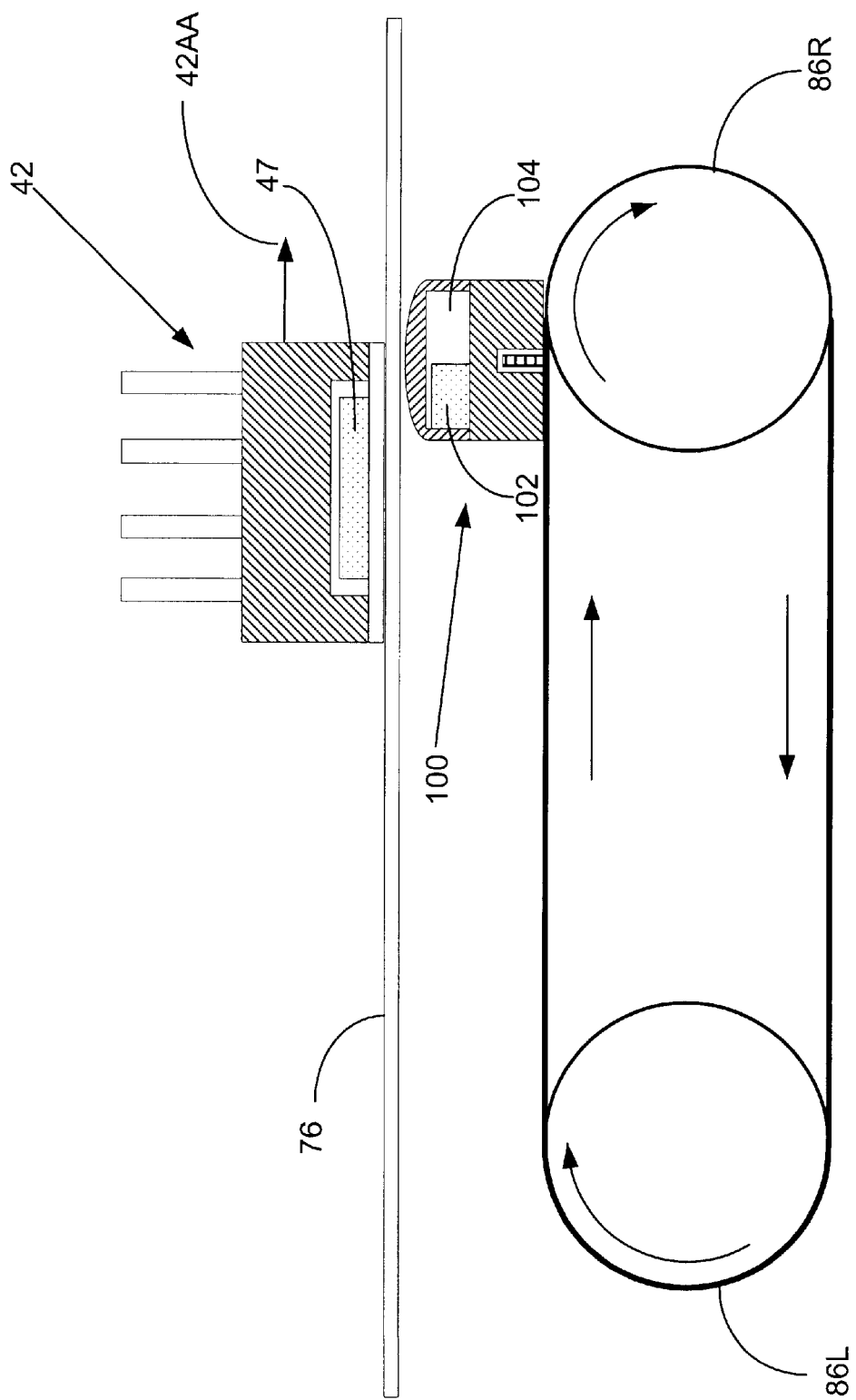
FIG. 12 is schematic elevation view of the magnetic drive system of FIG. 4 illustrating the sample rack of FIG. 5 in a moving stage as provided by the present invention.
Figure 13:
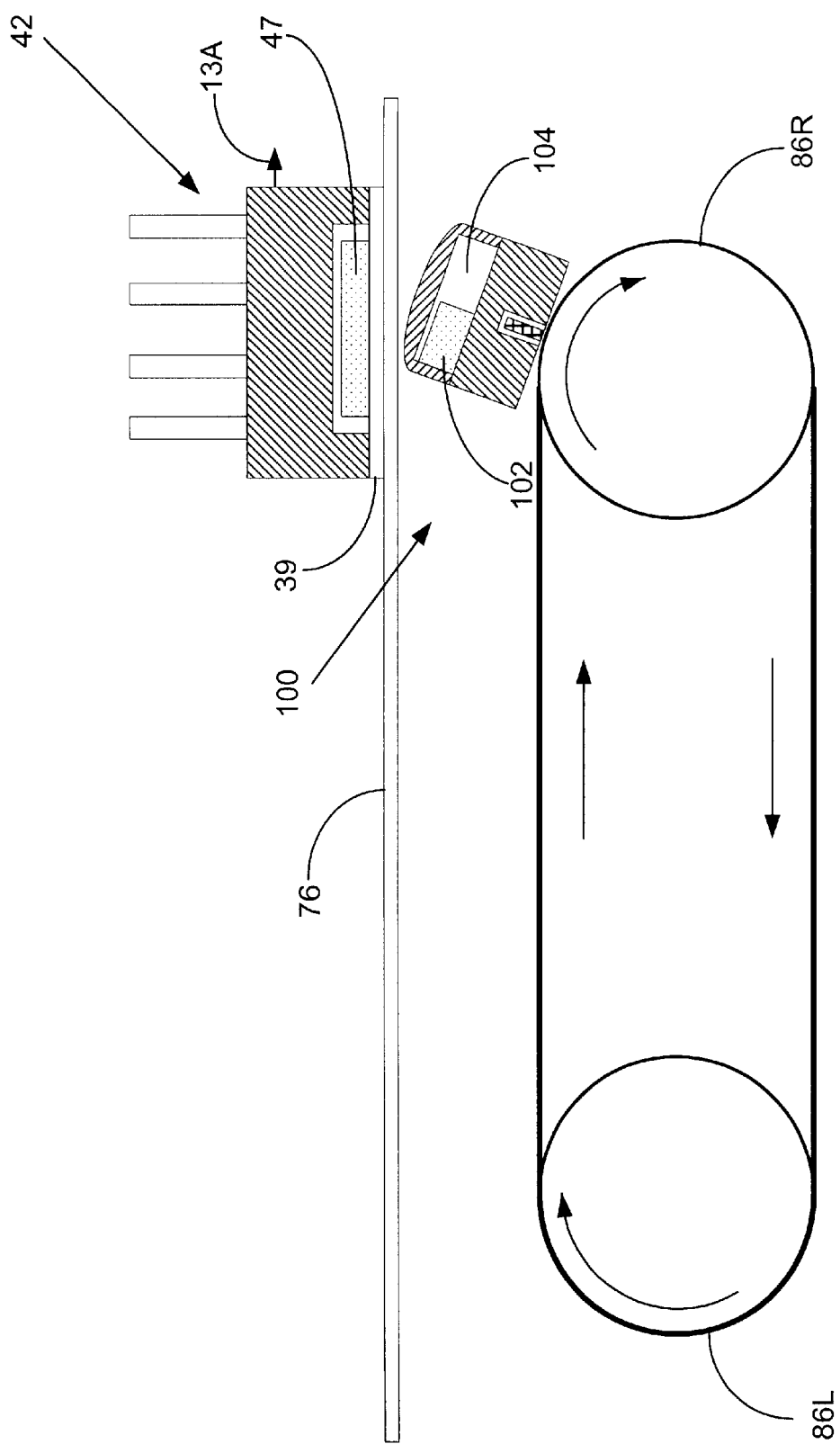
FIG. 13 is schematic elevation view of the magnetic drive system of FIG. 4 illustrating the transition of the sample rack of FIG. 5 from a moving stage to a stationary position as provided by the present invention.
Figure 14:
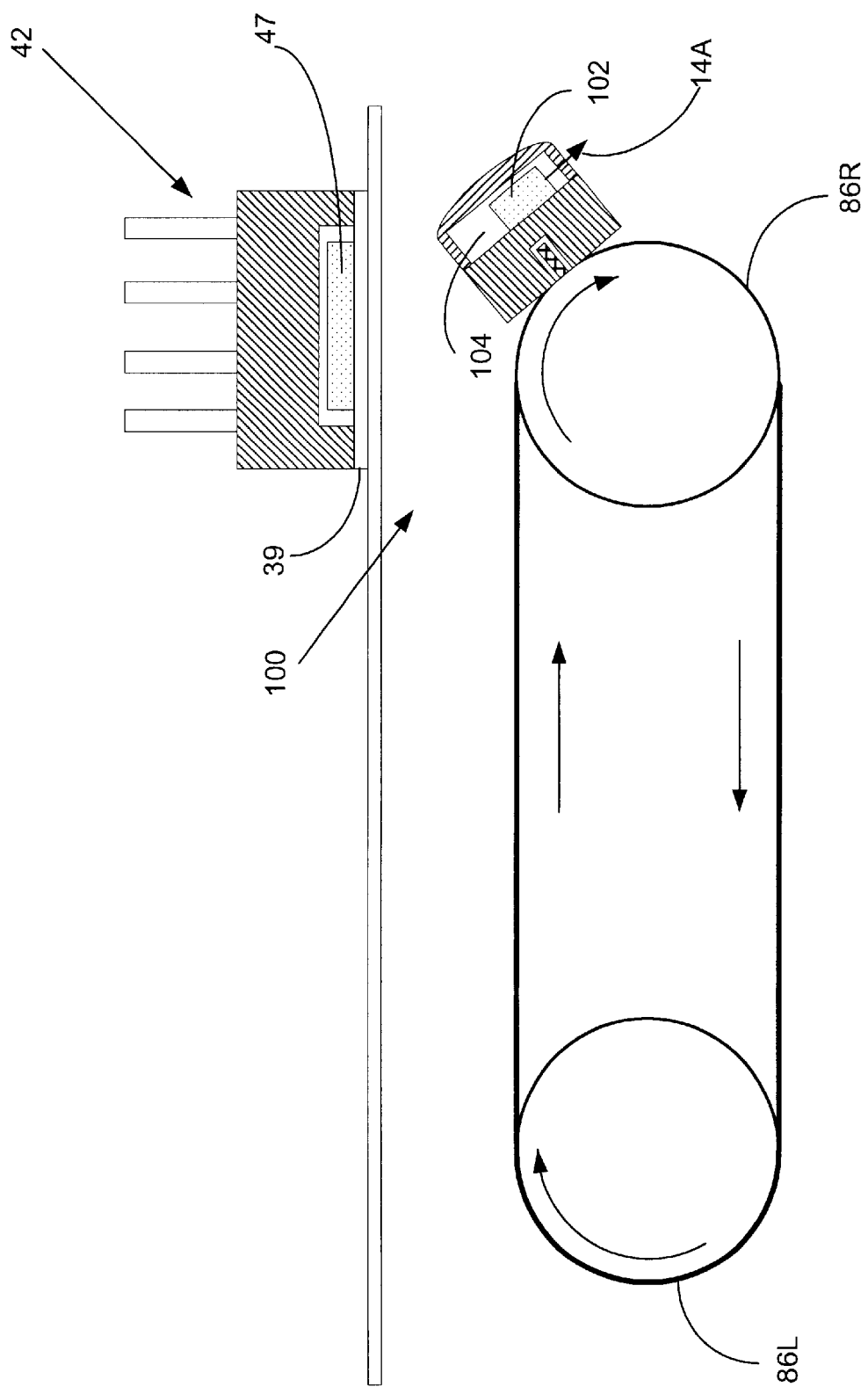
FIG. 14 is schematic elevation view of the magnetic drive system of FIG. 4 illustrating the sample rack of FIG. 5 in a stationary position as provided by the present invention.

Continued movement of belt 85 supporting magnetic housing 100 maintains sample rack 42 in a continuously moving state along surface 76, as indicated by a relatively longer arrow 42AA in FIG. 12, until housing 100 approaches pulley 86R located at the opposite end of surface 76, illustrated in FIG. 13. As may be seen in FIGS. 13–15, a situation related to but opposite that described hereinabove is created and the sample rack 42 is next smoothly and continuously transitioned from a moving state to a stationary position, thereby further ensuring that the potential for fluid spillage or damage is minimized.

Figure 15:
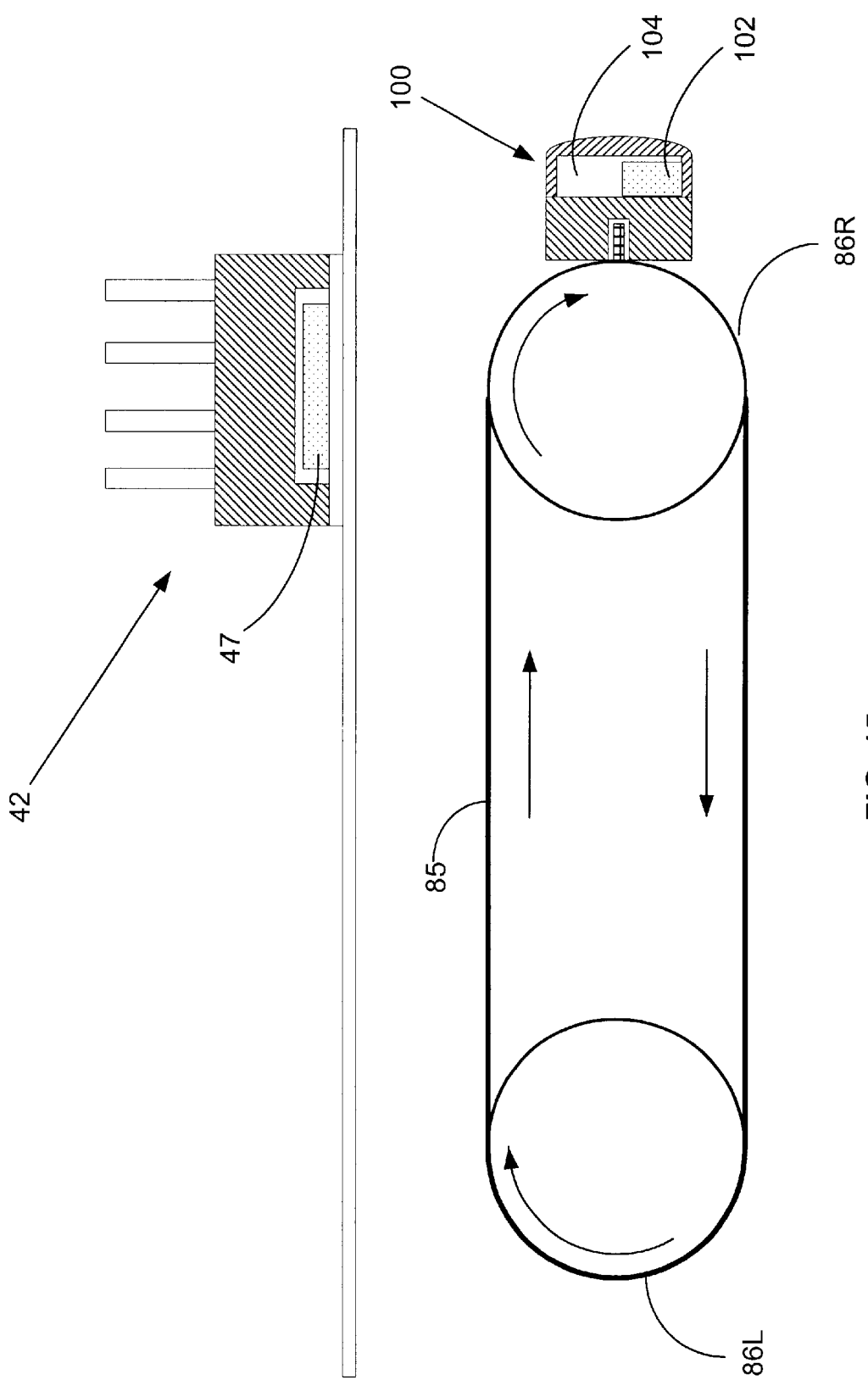
FIG. 15 is schematic elevation view of the magnetic drive system of FIG. 4 illustrating the sample rack of FIG. 5 and the magnetic housing of FIG. 6 in the final of a series of illustrations of the present invention in use.

In FIG. 13, as housing 100 begins to be rotated clock-wise around pulley 86R, the physical separation between magnet 102 and plate 47 begins to increase beyond that minimum distance corresponding to maximum magnetic interactions between magnet 102 and plate 47 seen in FIGS. 10–12. Consequently, magnetic forces acting on plate 47 in rack 42 begin to slowly decrease and movement of rack 42 begins to slowly decrease, as indicated by relatively shorter arrow 13A. As housing 100 is moved further by belt 84 around pulley 86, like seen in FIG. 14, the physical separation between magnet 102 and plate 47 continues to increase so that magnetic interactions between magnet 102 and plate 47 slowly and continuously decrease to a value that is ineffective in producing further movement of rack 42, thereby smoothly and continuously transitioning rack 42 from a moving state to a stationary position. As may also be seen in FIG. 14 and indicated by arrow 14A, magnet 102 is pulled by gravity towards the right-side of cavity 104, so that rack 42 slowly transitions from a moving state to a fully stationary position, indicated by the absence of an arrow attached to rack 42. Finally, as seen in FIG. 15, housing 100 is finally moved further around pulley 86 until cavity 104 is in a vertical orientation and magnet 102 rests against the right-side of cavity 104.

As mentioned earlier, a key and desirable feature of the present invention is the magnetic sample transport system 10 being capable of bi-directional movement of sample racks 10 along a single one of either input lane 72 or output lane 74 without the necessity for different or additional mechanisms to safely transition rack 42 from a stationary position to a moving state. In operation of transport system 10, FIG. 15 is the reversal of FIG. 8 so that sample rack 42 may be transitioned from a stationary position to a moving state, moving from right-to-left using the same principles of operation shown in FIGS. 8–14.

Figure 16:
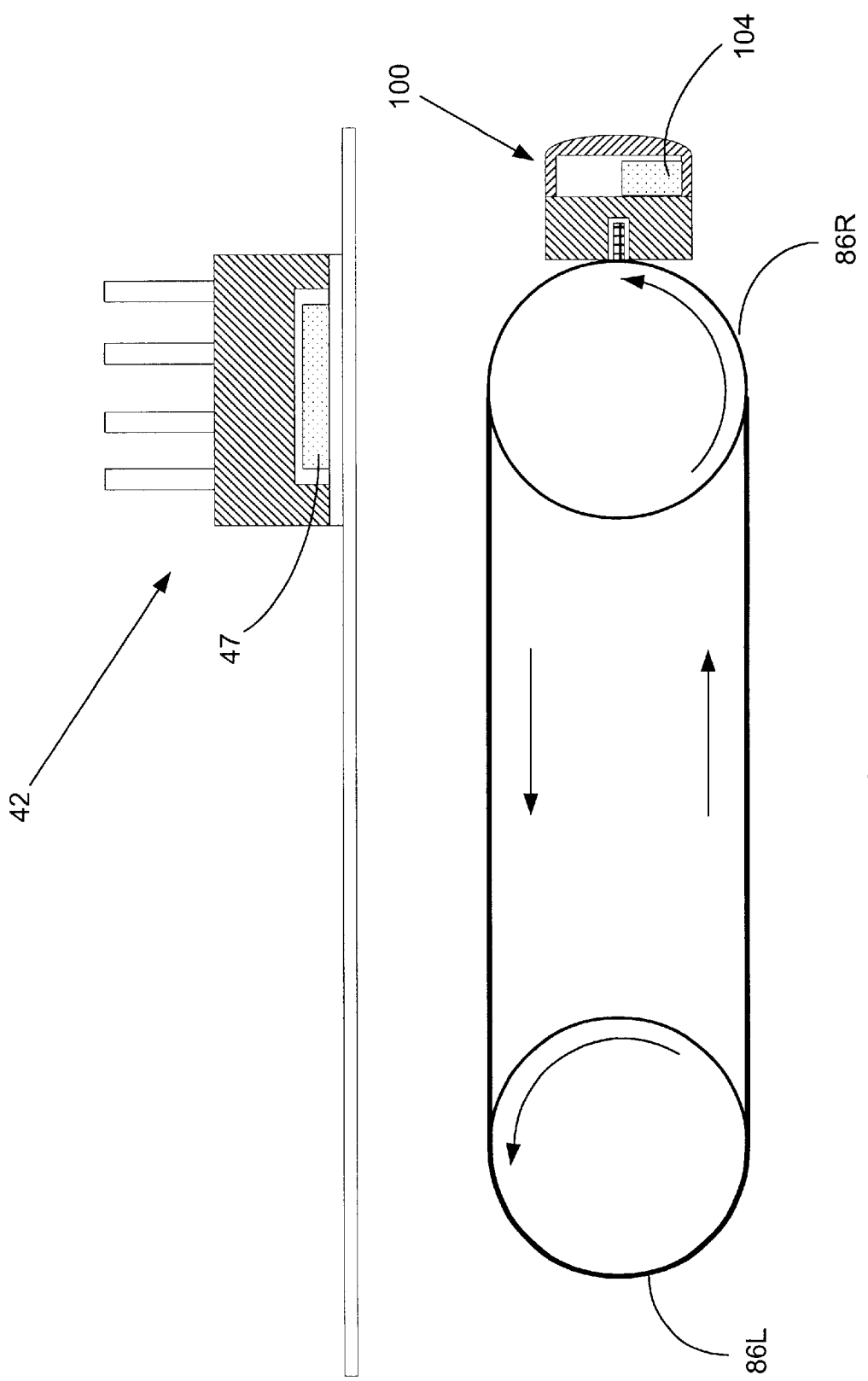
FIG. 16 is schematic elevation view of the magnetic drive system of FIG. 4 illustrating bi-directional movement of sample racks along either an input or output lane without the necessity for additional mechanisms; and, FIG. 17 is a graphical representation of relative magnetic interactions between the sample rack of FIG. 5 and the magnetic housing of FIG. 6 as provided by the present invention.

As may be seen by examining FIG. 16, such an objective may be achieved by simply reversing the direction of rotation of pulleys 86R and 86L, without an interchange of parts or additional features, as depicted in FIG. 16. In addition, as described in the alternate embodiment of FIG. 3A, a single input-output lane 72/74 may be formed along operating surface 76, and when taken with a single bi-directional magnetic drive system 90, racks 42 may be moved from a load/unload position 72L/U at a first end of the input-output lane 72/74 right-to-left along the length of input-output lane 72/74 and returned to load/unload position 72L/U after aspiration is completed.

Figure 17:
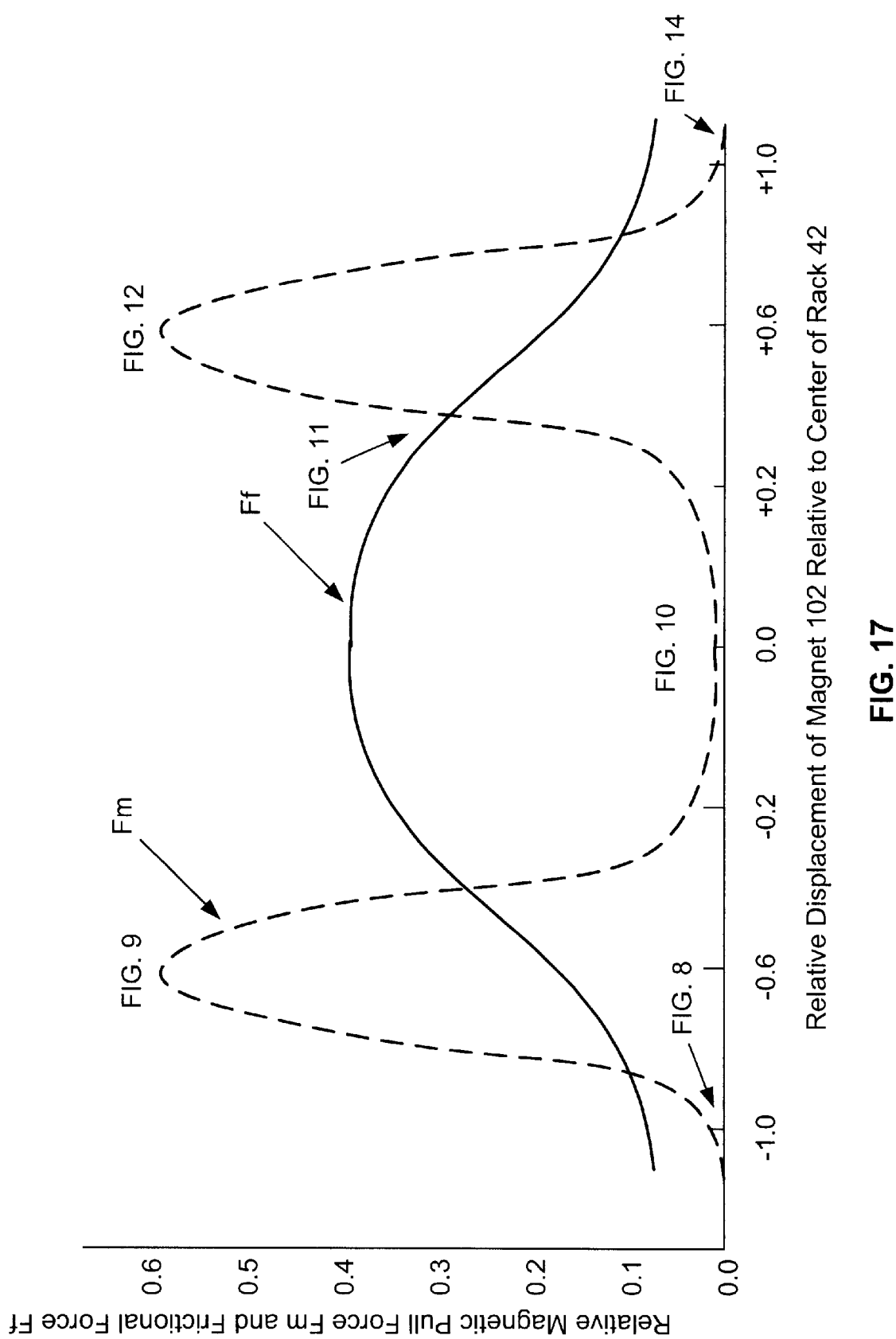

Corresponding to FIG. 12, in the central portion of the graph of FIG. 17, it is the maximum relative magnetic field strength between plate 47 and magnet 102 that causes the greatest movement of rack 42 along the plate. 76 as belt 85 is driven by pulleys 86L and 86R. Similarly, in the rightmost portion, corresponding to FIGS. 13–15, the relative strength of magnetic interaction between plate 47 and magnet 102 is slowly and continuously decreased from a maximum relative magnetic field strength (in producing movement of rack 42) to essentially an ineffective interaction, corresponding to FIG. 15, resulting in a smooth and continuous transition of rack 42 from a moving state to a stationary position.

FIG. 17 is a graphical schematic representation of the different instances described above as rack 42 is transitioned first from a stationary position to a moving state and back to a stationary position. The strength of the magnetic field interaction between magnet 102 and plate 47 is illustrated as a dashed line, Fm, as function of the displacement of magnet 102 relative to the center of rack 42. The strength of restraining frictional forces between rack 42 and operating surface 76 is illustrated as a solid line, Ff, also as function of the displacement of magnet 102 relative to the center of rack 42 so as to overlay the "pulling force" and the "restraining force" acting on rack 42.

The leftmost portion of FIG. 17 corresponds to the initial absence of a pulling magnetic force, depicted in FIG. 8. As the relative strength of magnetic interaction between plate 47 and magnet 102, indicated by curve Fm, is slowly and continuously increased to a maximum relative magnetic field strength, corresponding to FIG. 9, magnet 102 "jumps" rightwards inside cavity 104. The central portion of FIG. 17 corresponds to FIG. 10 where magnet 102 has initially moved underneath plate 47; the "pulling force Fm" then increases until exceeding the "restraining force" Ff and movement of the rack 42 commences, FIG. 11. After movement of rack 42 commences, the frictional forces Ff smoothly decrease and the "pulling force Fm" increases, causing a smooth and continuous transition of rack 42 to the moving state depicted in FIG. 12. Finally, as the magnetic interaction, curve Fm, is decreased in accord with FIG. 13, the magnetic force Fm slowly falls below the frictional forces Fr contributing to a smooth and continuous transition of rack 42 from a moving state to a stationary position.

It will be appreciated by those skilled in that art that a number of design variations may be made in the above essence of the present invention wherein magnetic housings are smoothly and continuously moved proximate a magnetic sample rack so that magnetic forces emanating from the housing magnet overcome frictional resistive forces between the sample racks and the operating surface and move the sample racks along input and output lanes defined in the operating surface. One such alternate embodiment would employ a rotating arm attached to the linear transport mechanism with a magnet at the end of the arm. As the magnet approaches the sample rack, the magnet would rotate to a position under the rack. Thus a rotational motion takes the place of sliding motion described above. In both instances, abrupt movements of the sample racks are eliminated because the housing magnet slides smoothly underneath a plate secured in a sample rack, secures the sample rack, and pulls the rack from a first stationary position along the operating surface to a moving state as the housings are moved at a steady rate by a pulley driven belt. Consequently, the sample rack smoothly transitions from a stationary position to a moving state, thereby minimizing the potential for fluid spillage from an open sample container. Similarly, the housing magnet slides smoothly away from the sample rack, releases the sample rack, and changes the rack from a moving state to a second stationary position along the operating surface as the housing is moved at a steady rate by a pulley driven belt. In an obvious alternate embodiment, plate 47 in base cavity 42C of sample rack 42 could be made to be moveable by enlarging the cavity 42C and magnet 102 in housing 100 could be made stationary and the advantages of the present invention still be achieved. Variations in the magnetic field strength of the housing magnet, the magnetic susceptibility of the rack plate, the size and weight of a loaded sample rack, frictional characteristics of operating surface, and base sheet may easily be modified to achieve the desired operating characteristics described above. For these reasons, the present invention is not limited to those embodiments precisely shown and described in the specification but only by the following claims.

We claim:

1. A method of transitioning a sample rack along an operating surface from a stationary position to a moving state by:

locating a magnetic conveyor system beneath the operating surface, the conveyor system comprising a plurality of magnetic housings attached to a linear drive mechanism, the magnetic housings including a magnet slideably contained therein;

providing a sample rack having an upper portion and a lower portion on the operating surface, the rack adapted to support one or more containers containing a liquid sample in the upper portion, the rack having a ferromagnetic plate secured in a closed base cavity in the lower portion;

placing the sample rack on the operating surface with the lower portion in contact with the operating surface; and, moving the magnetic housings in a single direction beneath the operating surface by activating the pulley driven belt, wherein the magnetic housings are distanced from the magnetic sample rack so that magnetic forces emanating from the slideable magnet and acting on the ferromagnetic plate are sufficiently strong so as to overcome resistive forces between the sample rack and the operating surface and move the sample racks along the operating surface in concert with the activated belt.

2. The method of claim 1 wherein each of said magnetic housings comprise a lower portion attached to the drive mechanism and a closed upper portion containing the slideable magnet.

3. The method of claim 2 wherein said slideable magnet moves from a first position to a second position in the closed upper portion, the first position being located a relatively greater distance from the sample rack and the second position is located a relatively smaller distance from the sample rack in response to the drive mechanism being activated.

4. The method of claim 2 wherein said sample rack is transitioned from a stationary position to a moving state after the slideable magnet is moved to the second position.

5. The method of claim 1 wherein said linear drive mechanism is bi-directional.

6. The method of claim 1 wherein said linear drive mechanism comprises a pulley driven belt.

7. The method of claim 1 wherein said containers are open.

8. A method of transporting a sample rack along a operating surface in either of two opposed directions by:

locating a magnetic conveyor system beneath the operating surface, the conveyor system comprising a plurality of magnetic housings attached to a linear drive mechanism, the magnetic housings including a magnet slideably contained therein;

providing a sample rack having a ferromagnetic plate secured in a closed base cavity in the lower portion;

placing the sample rack on the operating surface with the lower portion in contact with the operating surface;

moving the magnetic housings in a first direction beneath the operating surface by activating the linear drive mechanism in said first direction, wherein the magnetic housings are distanced from the magnetic sample rack so that magnetic forces emanating from the slideable magnet and acting on the ferromagnetic plate are sufficiently strong so as to overcome resistive forces between the sample rack and the operating surface and move the sample racks along the operating surface in concert with the activated linear drive mechanism, and wherein the slideable magnet moves from a first position to a second position in the closed upper portion, the first position being located a relatively smaller distance from the sample rack and the second position is located a relatively large distance from the sample rack while the pulley driven belt is activated; and, moving the magnetic housings in a second direction opposite to said first direction by reversing the linear drive mechanism so as to move said magnetic housings in said second direction.

9. The method of claim 8 wherein the sample rack is transitioned from a stationary position to a moving state after the slideable magnet is moved to the second position.

10. The method of claim 1 wherein said the operating surface has a friction-reducing layer applied thereover.

11. The method of claim 8 wherein said the operating surface has a friction-reducing layer applied thereover.

* * * * *